United States Patent
Korenberg et al.

(10) Patent No.: US 10,478,436 B2
(45) Date of Patent: *Nov. 19, 2019

(54) APPLICATION OF 5-HT6 RECEPTOR ANTAGONISTS FOR THE ALLEVIATION OF COGNITIVE DEFICITS OF DOWN SYNDROME

(71) Applicant: The University of Utah Research Foundation, Salt Lake City, UT (US)

(72) Inventors: Julie Ruth Korenberg, Los Angeles, CA (US); Karen Sue Wilcox, Sandy, UT (US); Peter Jeffrey West, Bountiful, UT (US); Raymond Pierre Kesner, Salt Lake City, UT (US)

(73) Assignee: THE UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/681,312

(22) Filed: Apr. 8, 2015

(65) Prior Publication Data

US 2015/0209353 A1    Jul. 30, 2015

Related U.S. Application Data

(63) Continuation of application No. 13/837,887, filed on Mar. 15, 2013, now Pat. No. 9,029,379, which is a continuation-in-part of application No. PCT/US2012/000464, filed on Oct. 3, 2012.

(60) Provisional application No. 61/681,555, filed on Aug. 9, 2012, provisional application No. 61/626,781, filed on Oct. 3, 2011.

(51) Int. Cl.

| *A61K 31/505* | (2006.01) |
| *A61K 31/404* | (2006.01) |
| *A61K 31/4745* | (2006.01) |
| *A61K 31/4045* | (2006.01) |
| *A61K 31/454* | (2006.01) |
| *A61K 31/495* | (2006.01) |
| *A61K 31/4985* | (2006.01) |
| *A61K 31/506* | (2006.01) |
| *A61K 45/06* | (2006.01) |
| *C07D 209/14* | (2006.01) |
| *C07D 239/50* | (2006.01) |
| *C07D 295/096* | (2006.01) |
| *C07D 401/04* | (2006.01) |
| *C07D 401/10* | (2006.01) |
| *C07D 487/04* | (2006.01) |
| *A61K 31/496* | (2006.01) |

(52) U.S. Cl.
CPC .......... *A61K 31/505* (2013.01); *A61K 31/404* (2013.01); *A61K 31/4045* (2013.01); *A61K 31/454* (2013.01); *A61K 31/4745* (2013.01); *A61K 31/495* (2013.01); *A61K 31/496* (2013.01); *A61K 31/4985* (2013.01); *A61K 31/506* (2013.01); *A61K 45/06* (2013.01); *C07D 209/14* (2013.01); *C07D 239/50* (2013.01); *C07D 295/096* (2013.01); *C07D 401/04* (2013.01); *C07D 401/10* (2013.01); *C07D 487/04* (2013.01)

(58) Field of Classification Search
CPC .. C07D 209/14; C07D 239/50; C07D 295/06; C07D 401/04; C07D 401/10; C07D 487/04; A61K 31/404; A61K 31/4045; A61K 31/454; A61K 31/4745; A61K 31/495; A61K 31/496; A61K 31/4985; A61K 31/505; A61K 31/506; A61K 45/06
See application file for complete search history.

(56) References Cited

U.S. PATENT DOCUMENTS

| 5,225,407 | A | | 7/1993 | Oakley |
| 5,453,425 | A | * | 9/1995 | Francois ............... A61K 31/519 514/259.41 |
| 6,100,289 | A | | 8/2000 | Cugola et al. |
| 6,403,792 | B1 | | 6/2002 | Lee et al. |
| 6,479,488 | B1 | | 11/2002 | Di-Fabio et al. |
| 6,911,477 | B2 | | 7/2005 | Villalobes et al. |
| 6,949,562 | B2 | | 9/2005 | Yohannes et al. |
| 7,001,900 | B2 | | 2/2006 | Jacobsen et al. |
| 7,105,532 | B2 | | 9/2006 | Rawlings et al. |
| 7,253,198 | B2 | | 8/2007 | Demont et al. |
| 7,452,888 | B2 | | 11/2008 | Ahmed et al. |
| 7,642,256 | B2 | | 1/2010 | Harrison et al. |
| 7,694,607 | B2 | | 4/2010 | Ishikawa et al. |
| 7,745,642 | B2 | | 6/2010 | Bradley et al. |

(Continued)

FOREIGN PATENT DOCUMENTS

| EP | 2020230 | 2/2009 |
| WO | WO 2006/037482 | 4/2006 |

(Continued)

OTHER PUBLICATIONS

Antonarakis et. al., Trends in Molecular Medicine, 2006, Elsevier, vol. 12(10), pp. 473-479.*
Capone et. al., Journal of Developmental and Behavioral Pediatrics, 2008, Lippincott Williams & Wilkins, vol. 29, pp. 106-116.*
Bymaster et. al., European Journal of Pharmacology, 2001, Elsevier, vol. 430, pp. 341-349.*
CAS STN, Risperidone, abstract, publ. Jan. 24, 1987.*
Gravius et. al., Behavioral Pharmacology, 2011, Wolters Kluwer, vol. 22(2), Abstract only (Year: 2011).*

(Continued)

*Primary Examiner* — Sarah Pihonak
(74) *Attorney, Agent, or Firm* — RMCK Law Group, PLC

(57) ABSTRACT

Methods for treating Down syndrome and improving cognitive function of a patient with an intellectual disability are disclosed. 5-hydroxytryptamine sub-receptor six (5-HT$_6$) receptor antagonists are provided for improving the cognition of a Down syndrome patient.

20 Claims, 11 Drawing Sheets

(56) References Cited

U.S. PATENT DOCUMENTS

| | | | |
|---|---|---|---|
| 7,790,758 B2 | 9/2010 | Andreotti et al. | |
| 7,951,958 B2 | 5/2011 | Brodney et al. | |
| 8,680,105 B2 | 3/2014 | Jordan et al. | |
| 2002/0094979 A1 | 7/2002 | Revill et al. | |
| 2004/0019064 A1* | 1/2004 | Wu | A61K 31/519 514/259.4 |
| 2004/0102481 A1* | 5/2004 | Filla | C07D 401/04 514/323 |
| 2004/0122076 A1* | 6/2004 | Bobb | A61K 31/403 514/415 |
| 2004/0132734 A1* | 7/2004 | Edwards | C07D 471/04 514/249 |
| 2005/0038117 A1 | 2/2005 | Kong | |
| 2005/0245504 A1* | 11/2005 | Corbett | A61K 31/439 514/214.01 |
| 2006/0069094 A1 | 3/2006 | Bonhaus et al. | |
| 2007/0049576 A1 | 3/2007 | Barlow et al. | |
| 2007/0249603 A1* | 10/2007 | Johnson | C07D 401/04 514/235.2 |
| 2008/0009475 A1 | 1/2008 | Garner et al. | |
| 2008/0171779 A1* | 7/2008 | De Bruin | A61K 31/415 514/403 |
| 2008/0176829 A1* | 7/2008 | Brandt et al. | C07D 498/04 514/211.1 |
| 2008/0311179 A1* | 12/2008 | Van Loevezijn | A61K 9/0019 424/449 |
| 2009/0082388 A1 | 3/2009 | Hacksell et al. | |
| 2009/0264457 A1 | 10/2009 | Codony-Soler et al. | |
| 2010/0009983 A1 | 1/2010 | Barlow et al. | |
| 2010/0041672 A1 | 2/2010 | Bruton et al. | |
| 2010/0056531 A1 | 3/2010 | Danca et al. | |
| 2010/0074955 A1 | 3/2010 | Buschmann et al. | |
| 2010/0120747 A1 | 5/2010 | Codony-Soler et al. | |
| 2010/0152141 A1 | 6/2010 | Gannon et al. | |
| 2010/0189646 A1* | 7/2010 | Ramakrishna | C07D 209/94 424/9.1 |
| 2010/0256106 A1* | 10/2010 | Pasternak | C07D 209/16 514/210.02 |
| 2011/0003836 A1 | 1/2011 | McKnight et al. | |
| 2013/0005709 A1 | 1/2013 | Nirogi et al. | |
| 2013/0210829 A1 | 8/2013 | Korenberg et al. | |

FOREIGN PATENT DOCUMENTS

| | | |
|---|---|---|
| WO | WO 2008/024914 | 2/2008 |
| WO | WO 2009/039460 | 3/2009 |
| WO | WO 2009/155024 | 12/2009 |
| WO | WO 2013/055386 A2 | 4/2013 |

OTHER PUBLICATIONS

Arnt et. al., International Journal of Neuropsychopharmacology, 2010, CINP, vol. 13, pp. 1021-1033 (Year: 2010).*
Gravius et. al., Behavioral Pharmacology, 2011, Lippincott Williams & Wilkins, vol. 22, pp. 122-135 (Year: 2011).*
European Extended Search Report, European Application No. 12840527. 1, dated Jul. 6, 2015, 9 pages.
Arnt et al. "LU AE58054, a 5-HT6 antagonist, reverses cognitive impairment induced by subchronic phencyclidine in a novel object recognition test in rats" International Journal of Neuropsychopharmacology (2010) 13, 1021-1033.
Costa et al., "Prospects for Improving Brain Function in Individuals with Down Syndrome" CNS Drugs Springer International Publishing Switzerland 2013.
Dykens et al. "Psychiatric and Behavior Disorders in Persons with Down Syndrome" Mental Retardation and Developmental Disabilities Research Reviews 13: 272-278 (2007).
Dykens et al. Mental Retardation and Developmental Disabilities Research Reviews 13: 272-278 (2007).
Fone, Kevin "An update on the role of 5-hydroxytryptamine6 receptor in cognitive function" Nuropharmacology 55 (2008) 1015-1022.
Giacobini, Ezio "Cholinesterase inhibitors: new roles and therapeutic alternatives" Pharmacological Research 50 (2004) 433-440.
Hirano et al., 'Procognitive 5-HT6 Antagonists in the Rat Forced Swimming Test: Potential Therapeutic Utility in Mood Disorders Associated with Alzheimer's Disease', Life Sciences (Elsevier) 84, pp. 558-562, 2009.
International Search Report in PCT/US2014/027737 dated Jul. 30, 2014.
International Search Report in PCT/US2014/032876 dated Aug. 27, 2014.
International Search Report in PCT/US2012/000464 dated Mar. 27, 2013.
King et al., "A role for the 5-HT1A, 5-HT4 and 5-HT6 receptors in learning and memory" Trends in Pharmacological Sciences vol. 29 No. 9 (482-492).
Liem-Moolenaar et al. "Central nervous system effects of the internation between risperidone (single dose) and the 5-HT6 antagonist SB742457 (repeated doses) in healthy men," BR J Clin Pharmcol. Jun. 1, 2011 (Jun. 1, 2011), vol. 71, No. 6, pp. 907-916.
Meffre et al., "5-HT6 receptro recruitment of mTOR as a mechanism for perturbed cognition in schizophrenia" EMBO Molecular Medicine (2012) 4, 1043-1056.
Nirogi et al., "Synthesis and Pharmacological Evaluation of Aryl Aminosulfonamide Derivaties as Potent 5-HT6 Receptor Antagonists", Bioorganics & Medical Chemistry Letters, vol. 20, No. 15, pp. 4440-4443, 2010.
Non-Final Office Action Issued in U.S. Appl. No. 13/837,887 dated Jun. 3, 2014.
Notice of Allowance Issued in U.S. Appl. No. 13/837,887 dated Jan. 8, 2015.
Pytliak et al., "Serotonin Receptors—From Molecular Biolofy to Clinical Applications" Physiol. Red. 60: 15-25 2011.
Quiedeville et al., "5-HT6 Receptor Antagonists as Treatment for Age-Related Cognitive Decline" Rev. Neurosci. 2014.
Response to Non-Final Office Action Filed in U.S. Appl. No. 13/837,887 dated Nov. 3, 2014.
Response to Restriction/Election Requirement Filed in U.S. Appl. No. 13/837,887 dated Mar. 31, 2014.
Restriction/Election Requirement Issued in U.S. Appl. No. 13/837,887 dated Jan. 31, 2014.
Romero et al., 'Eficacy of Selective 5-HT6 Receptor Ligands Determined by Monitoring 5-HT6 Receptor-Mediated cAMP Signaling Pathways', British Journal of Pharmacology, vol. 148, pp. 1133-1143, 2006.
Rosse et al., '5-HT6 Receptor Antagonists as Potential Therapeutics for Cognitive Impairment', Medicinal Chemistry 10, pp. 207-221, 2010.
Sleight et al., 'Characterization of Ro 04-6790 and RO 63-0563: Potent and Selective Antagonists at Human and Rat 5-HT6 Receptors', British Journal of Pharmacology, Vo. 124, pp. 556-562, 1998.
Wallace et al., 'Drug Targets for Cognitive Enhancement in Neuropsychiatric Disorders', Pharmacology, Biochemistry and Behavior 99, pp. 130-145, 2011.
Written Opinion in PCT/US2012/000464 dated Apr. 8, 2014.
Written Opinion in PCT/US2014/027737 dated Jul. 30, 2014.
Written Opinion in PCT/US2014/032876 dated Aug. 27, 2014.
Australian First Examination Report, Australian Application No. 2016204104, dated Jan. 9, 2017, 6 pages.
Australian First Examination Report, Australian Application No. 2014228260, dated Jan. 13, 2017, 6 pages.
European Partial Supplementary Search Report, European Application No. 14765593.0, dated Nov. 23, 2016, 6 pages.
European Extended Search Report, European Application No. 14765593. 0, dated Feb. 27, 2017, 11 pages.
European Examination Report, European Application No. 12840527. 1, dated Jul. 10, 2017, 4 pages.
Isaac et al., "6-Bicyclopiperazinyl-1-arylsulfonylindoles and 6-Bicyclopiperidinyl-1-arylsulfonylindoles Derivates as Novel, Potent, and Selective 5-$HT_6$ Receptor Antagonists," Bioorganic & Medicinal Chemistry Letters, 2000, vol. 10, Issue 15, pp. 1719-1721.

* cited by examiner

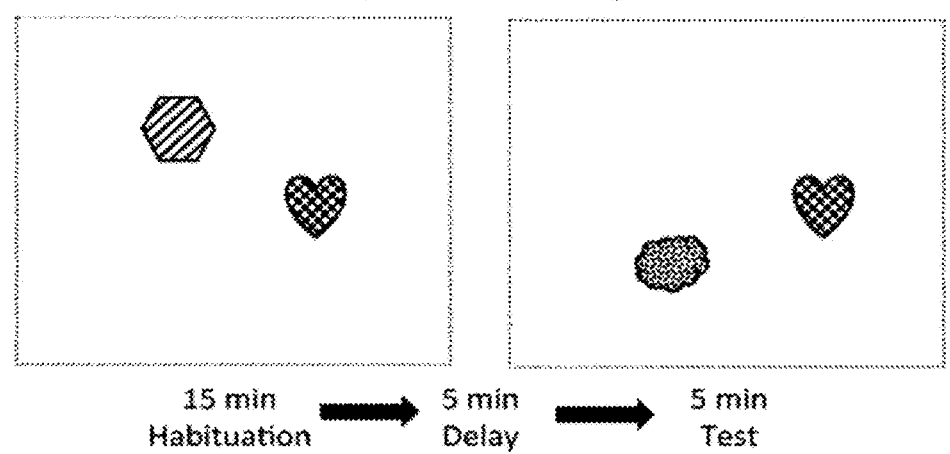

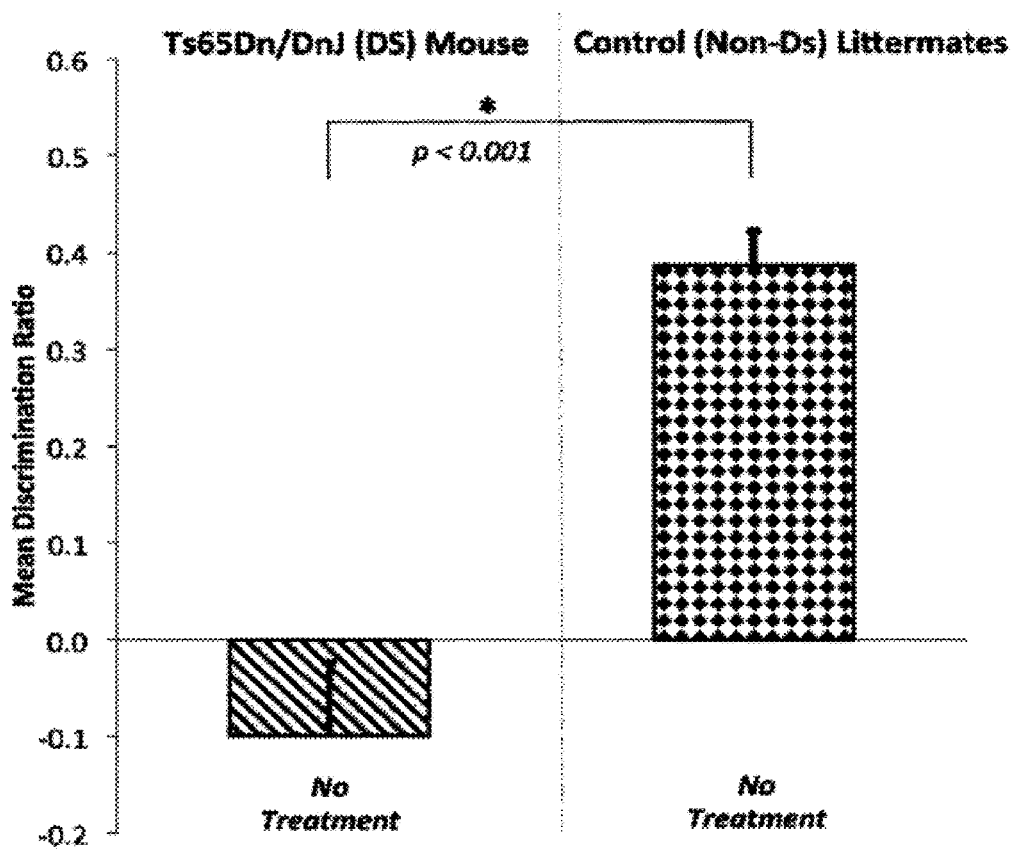

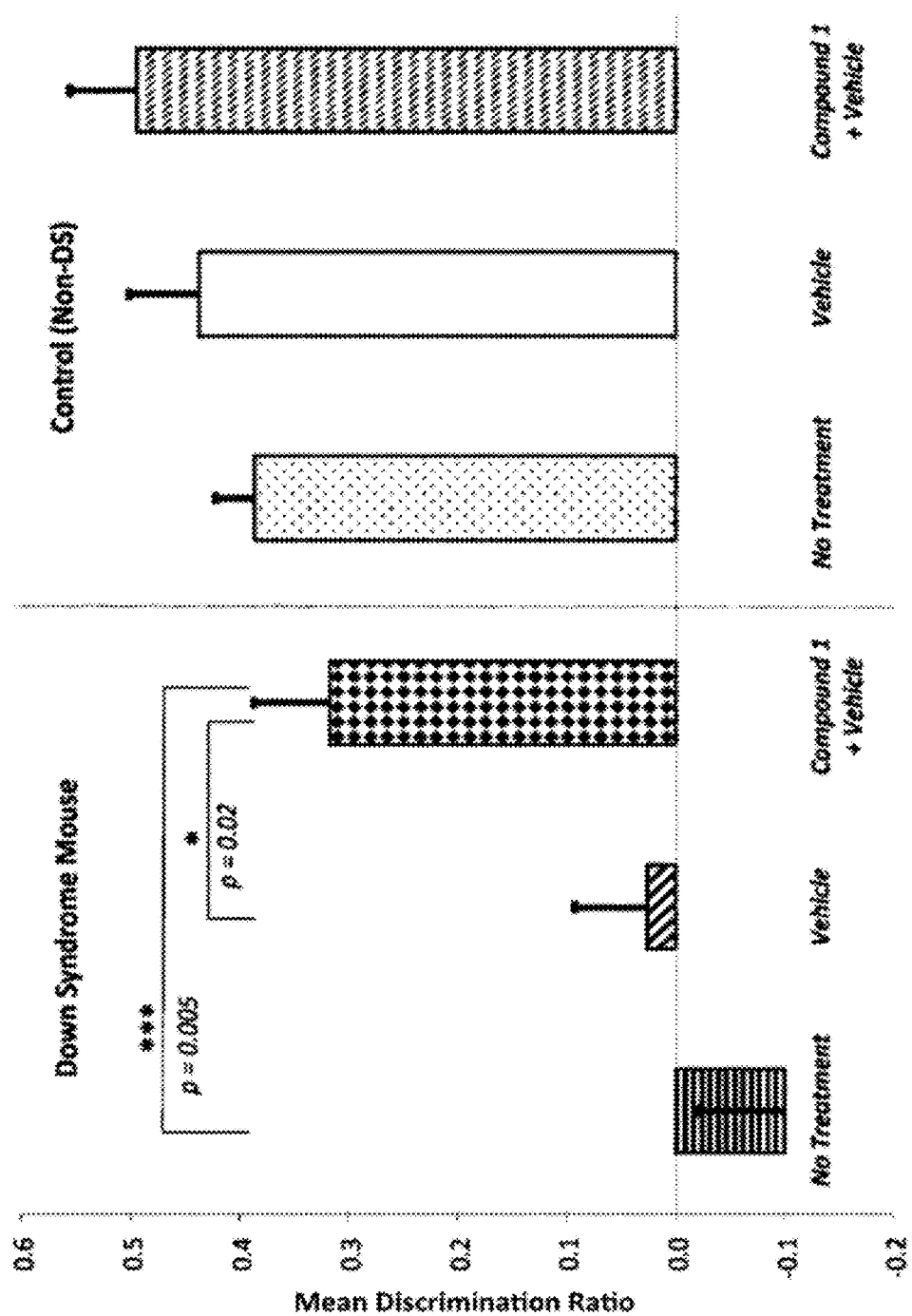

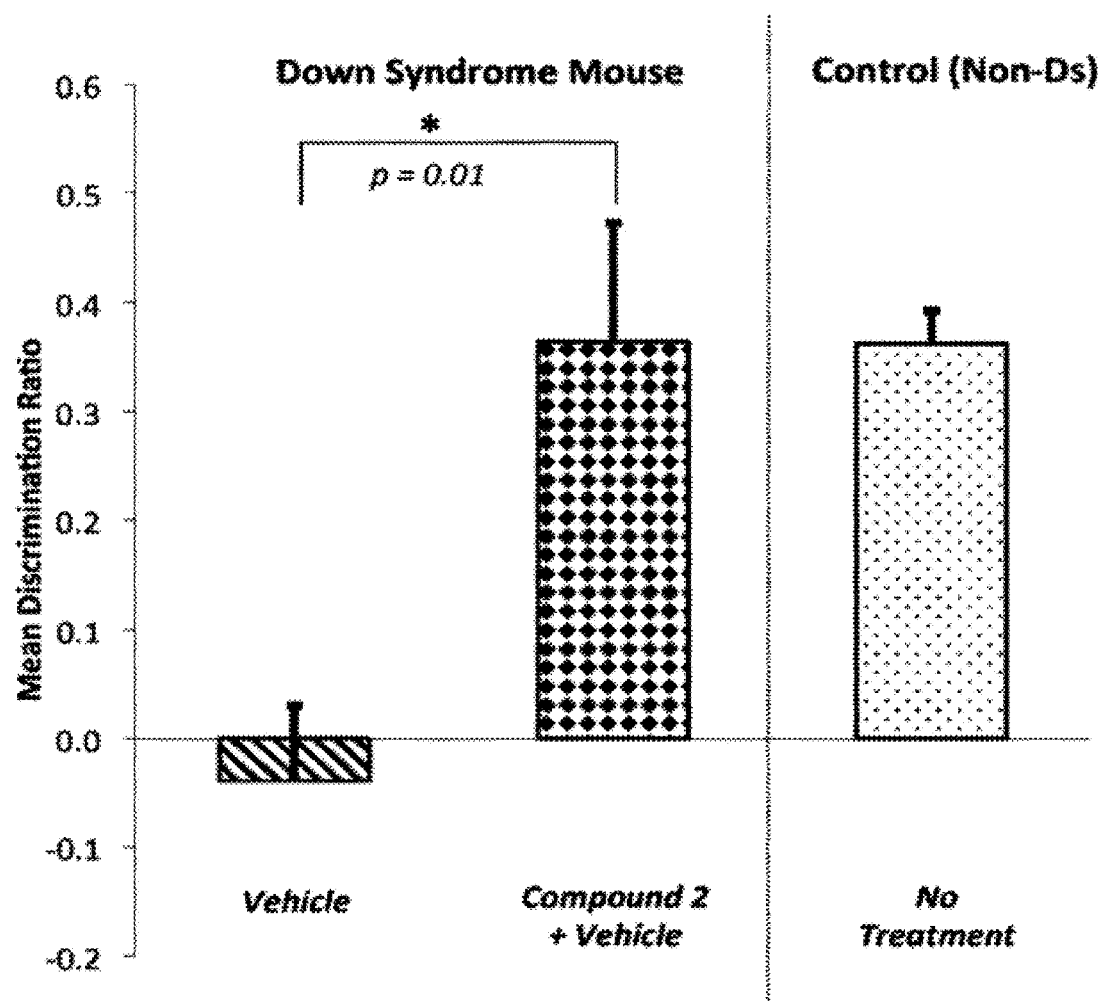

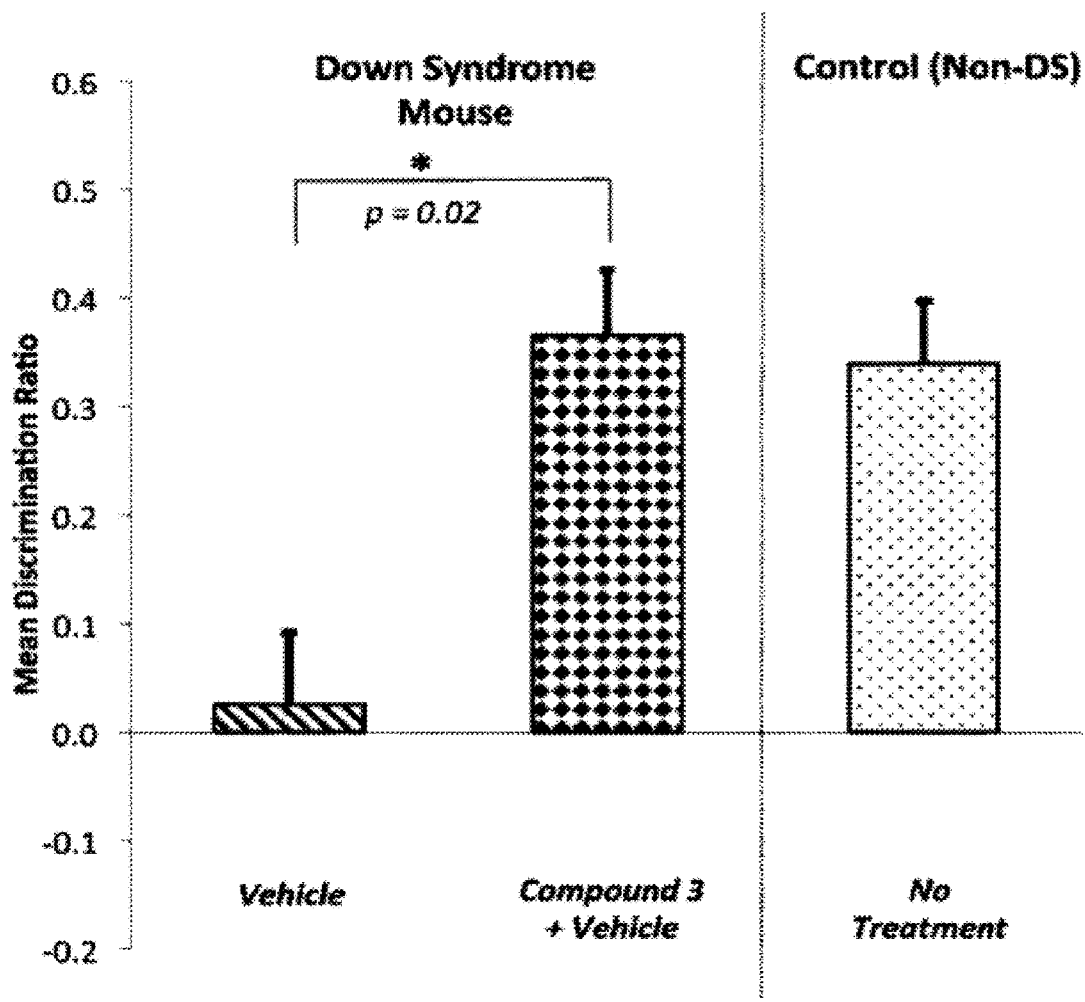

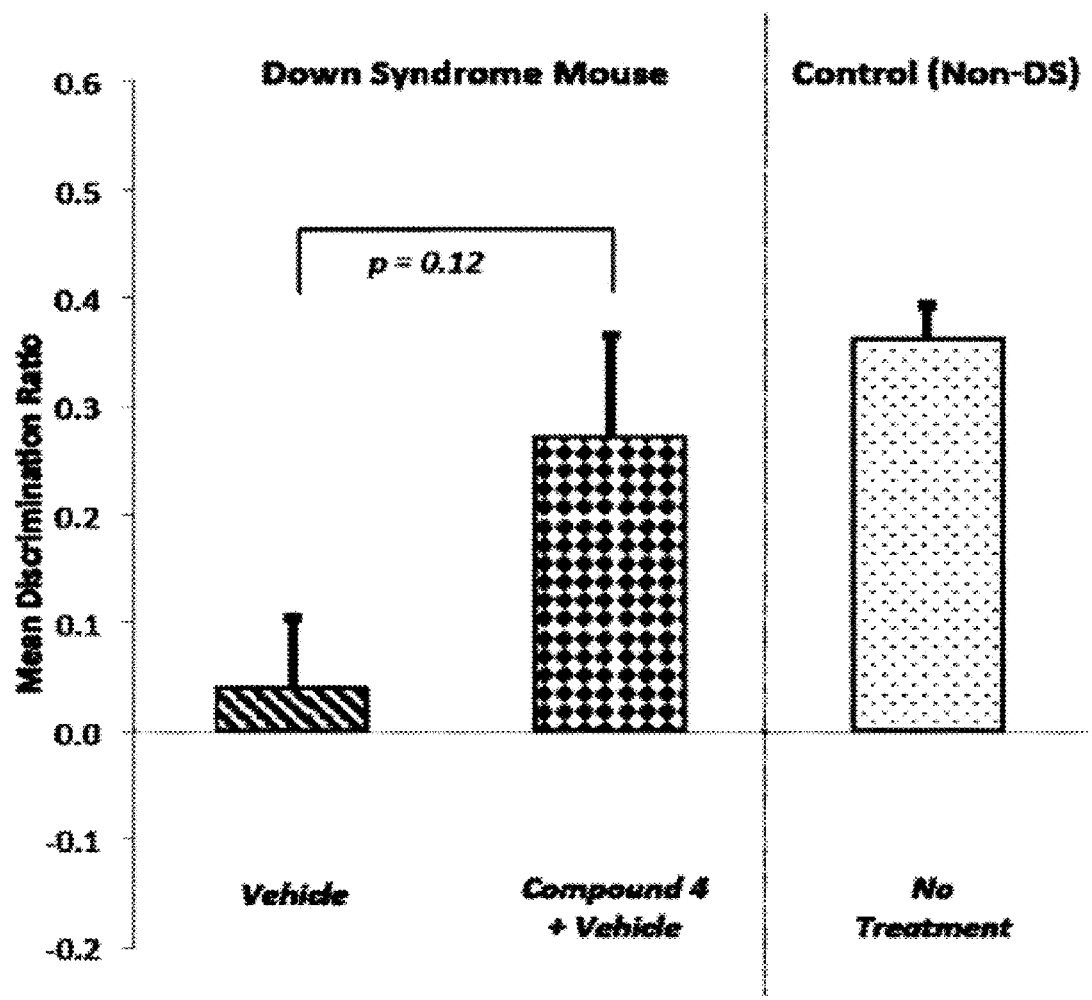

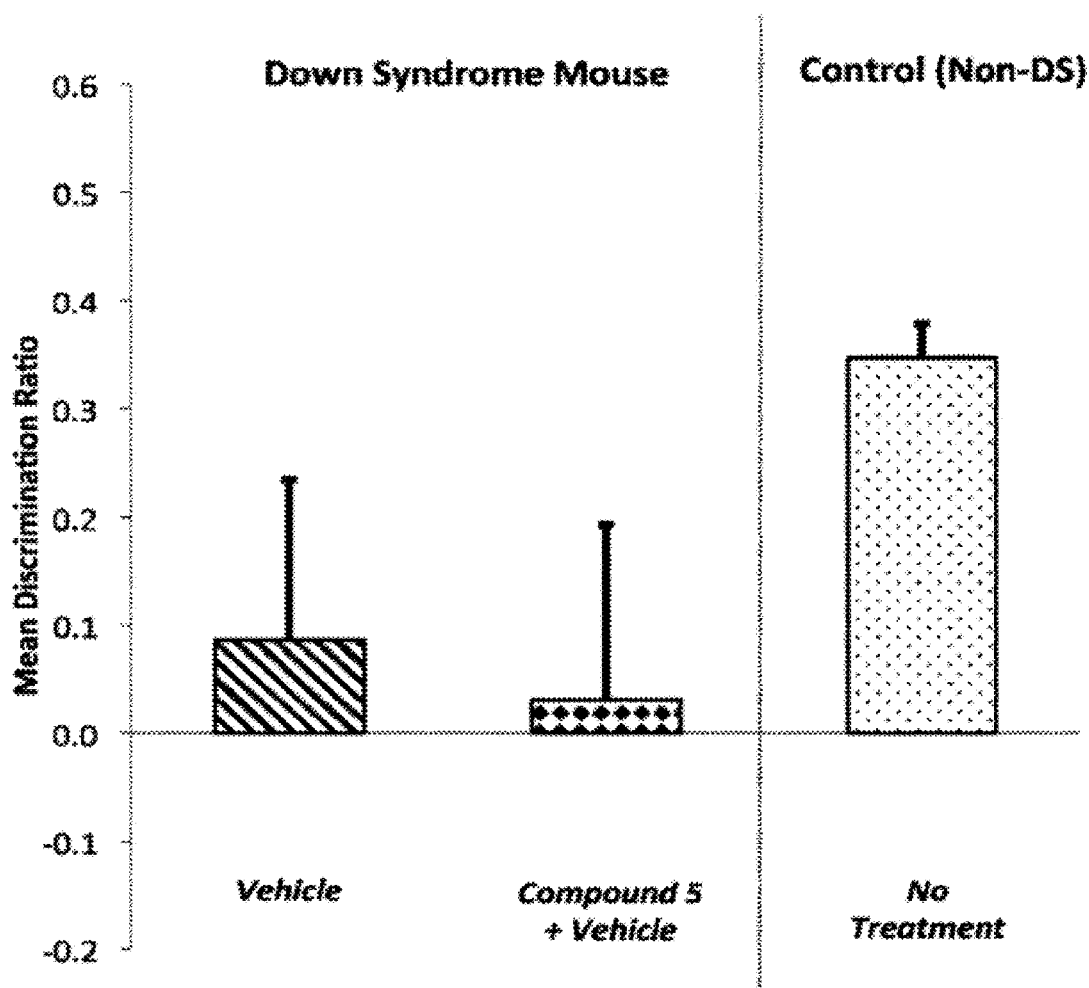

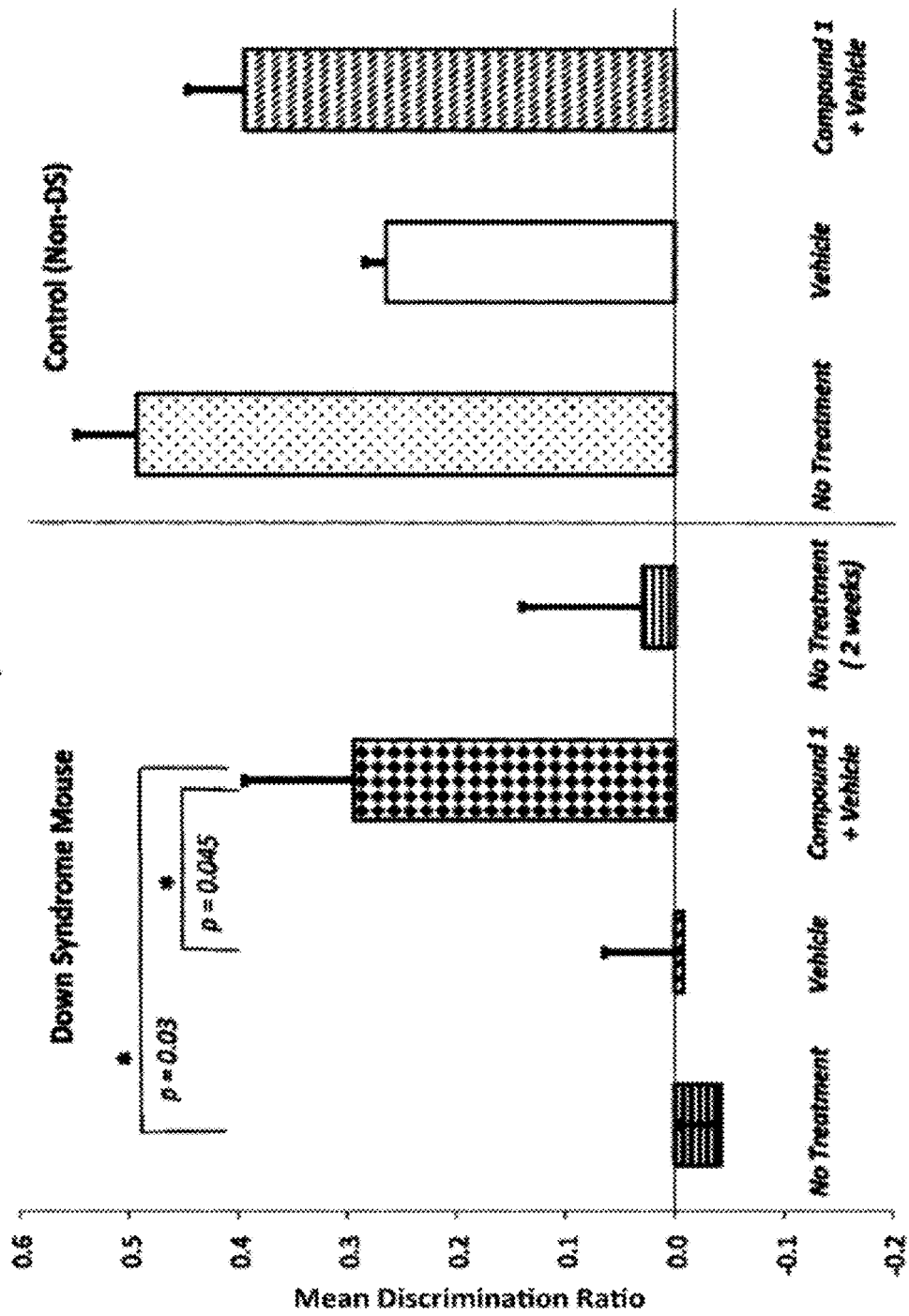

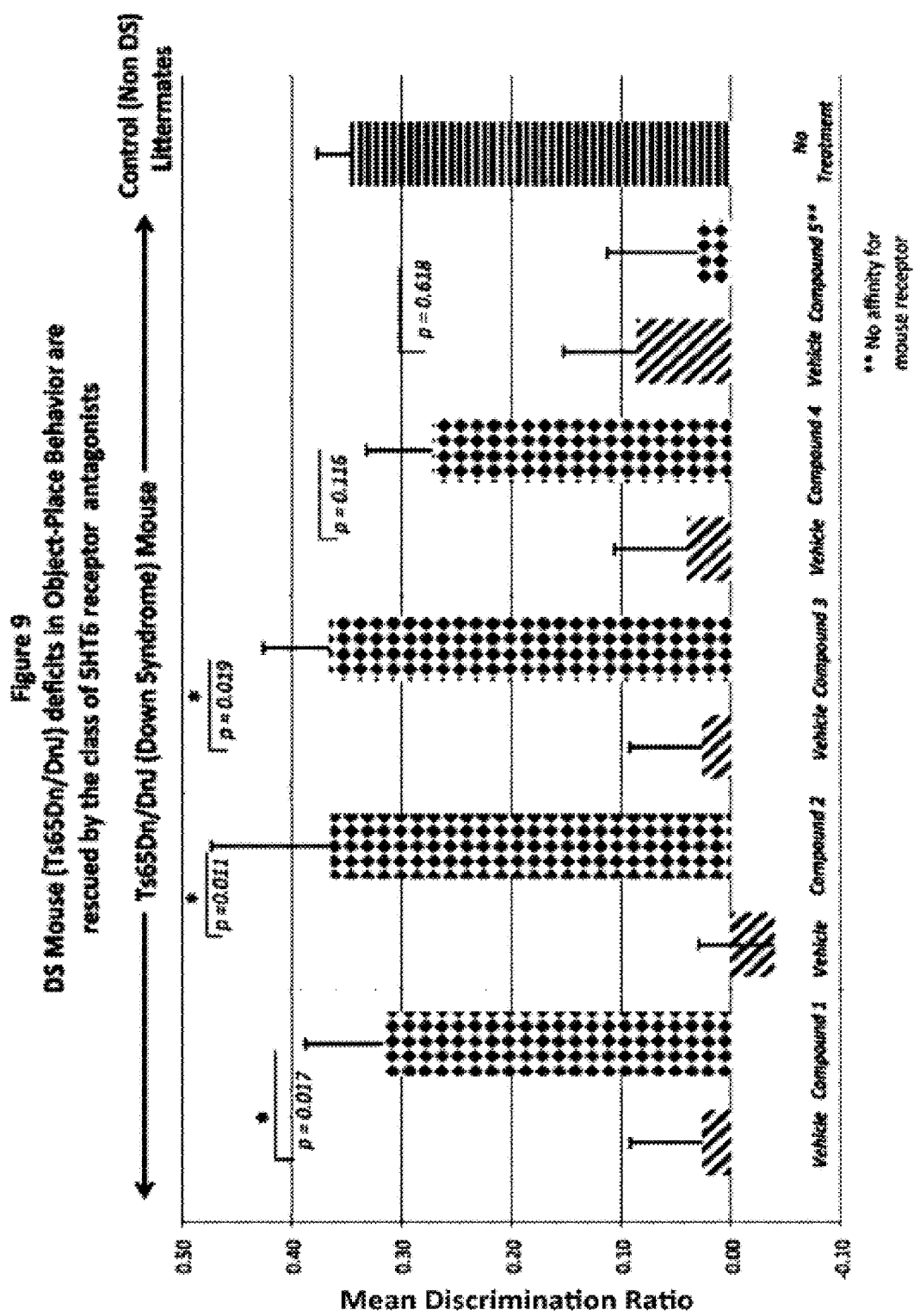

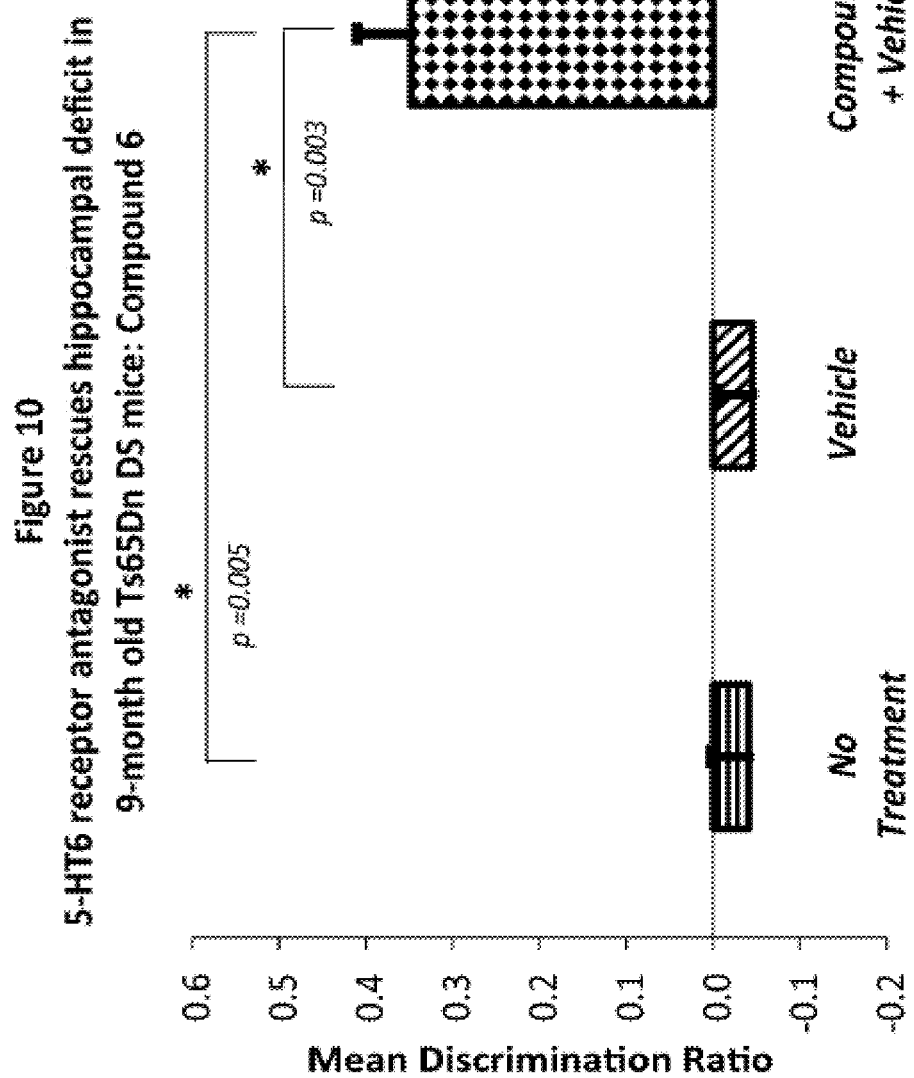

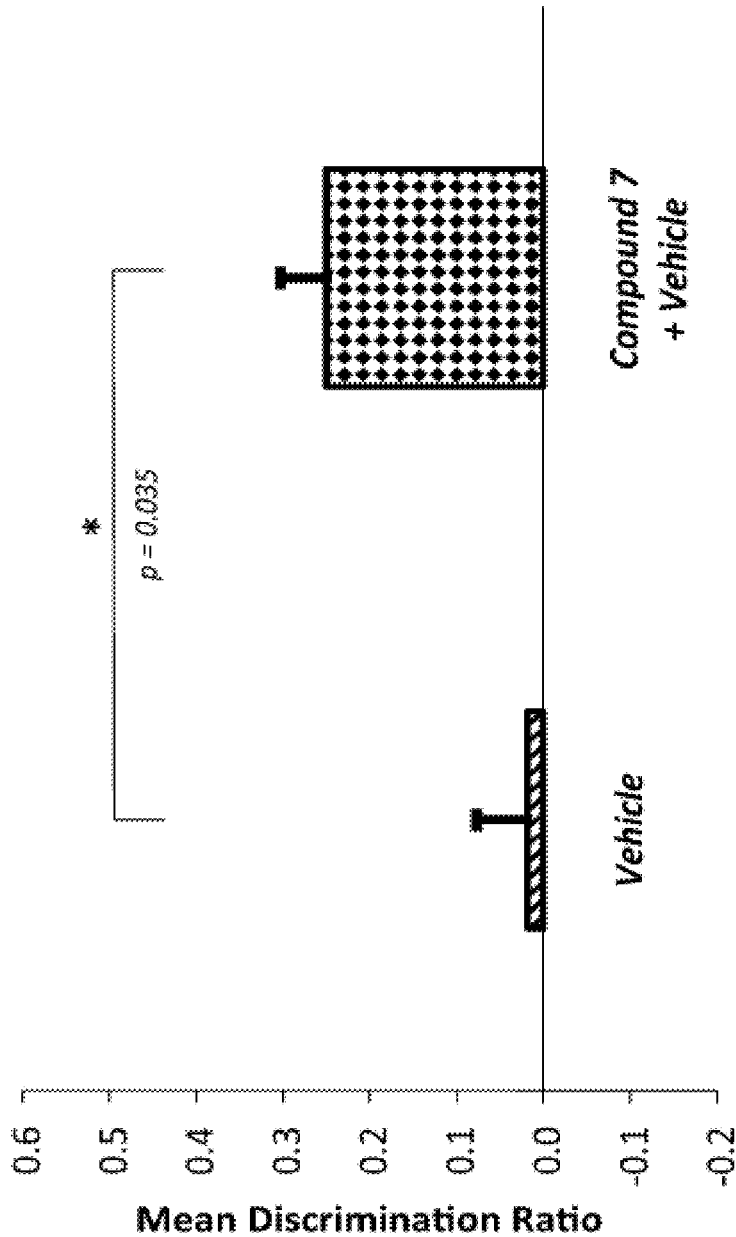

APPLICATION OF 5-HT6 RECEPTOR ANTAGONISTS FOR THE ALLEVIATION OF COGNITIVE DEFICITS OF DOWN SYNDROME

RELATED APPLICATIONS

The present application is a continuation of U.S. patent application Ser. No. 13/837,887, titled "Application of 5-HT$_6$ Receptor Antagonists for the Alleviation of Cognitive Deficits of Down Syndrome," which is a continuation-in-part of PCT Application No. PCT/US2012/000464, titled "Application of 5-HT$_6$ Receptor Antagonists for the Alleviation of Cognitive Deficits of Down Syndrome," filed Oct. 3, 2012, which claims priority to U.S. Patent Application No. 61/681,555, titled "Application of 5-HT$_6$ Receptor Antagonists for the Alleviation of Cognitive Deficits of Down Syndrome," filed Aug. 9, 2012, and U.S. Patent Application No. 61/626,781, titled "Rescue of Cognitive Deficits in the Down Syndrome Mouse Model Using a Novel Drug Treatment," filed Oct. 3, 2011, all of which are hereby incorporated by reference in their entireties.

TECHNICAL FIELD

The present disclosure relates generally to compounds and methods to improve cognitive disorders, such as Down syndrome. More specifically, the present disclosure relates to the use of class of compounds whose action relates to the binding or modification of structure or function of 5-HT6 receptor antagonists. Specific examples include: 4-amino-N-(2,6-bis(methylamino)pyrimidin-4-yl)benzenesulfonamide (compound 1); 2-(5-methoxy-2-phenyl-1H-indol-3-yl)-N,N-dimethylethanamine (compound 2); 2-(1-(naphthalen-1-ylsulfonyl)-1H-indol-6-yl)octahydropyrrolo [1,2-a]pyrazine (compound 3); 1-methyl-3-(1-methylpiperidin-4-yl)-1H-indol-5-yl 2,6-difluorobenzenesulfonate (compound 4), 4-amino-N-(2,6-bis(methylamino)pyrimidin-4-yl)benzenesulfonamide (compound 5), 2-(6-fluoro-1H-indol-3-yl)-N-(3-(2,2,3,3-tetrafluoropropoxy)benzyl)ethanamine (compound 6), and 3-(phenylsulfonyl)-8-(piperazin-1-yl)quinoline (compound 7), and to the usefulness of these and related compounds in the treatment of cognitive impairment accompanied with intellectual disabilities, those with an IQ of less than 85, those diagnosed with mental retardation, and, most specifically, those with Down syndrome.

BRIEF DESCRIPTION OF THE DRAWINGS

FIG. 1 is a diagram of an experimental paradigm, which is used to test hippocampal function and cognitive ability by determining how well a mouse is able to differentiate between a familiar object in a familiar location and a novel object in a novel location.

FIG. 2 is a graph comparing mean discrimination ratios for untreated Ts65Dn Down syndrome mice and untreated non-Ts65Dn (normal) mice (i.e., control mice).

FIG. 3 is a graph representing mean discrimination ratios of 3 to 4 month-old Down syndrome mice (i.e., Ts65Dn mice) and untreated non-Ts65Dn (normal) mice (i.e., control mice) that were treated with nothing, vehicle, and compound 1 with vehicle.

FIG. 4 is a graph representing mean discrimination ratios of Ts65Dn mice that were treated with vehicle, and compound 2 with vehicle, as well as untreated control mice.

FIG. 5 is a graph representing mean discrimination ratios of Ts65Dn mice that were treated with vehicle, and compound 3 with vehicle.

FIG. 6 is a graph representing mean discrimination ratios of Ts65Dn mice that were treated with vehicle, and compound 4 with vehicle.

FIG. 7 is a graph representing mean discrimination ratios of 8-month-old Ts65Dn mice and control mice that were administered with nothing, vehicle, and compound 1+vehicle.

FIG. 8 is a graph representing mean discrimination ratios of Ts65Dn mice that were administered with vehicle, and compound 5+vehicle.

FIG. 9 is a graph summarizing the mean discrimination ratios for the treatment of Ts65Dn mice treated with each of the compounds 1-5.

FIG. 10 is a graph representing mean discrimination ratios of 9-month-old Ts65Dn mice and control mice that were administered with nothing, vehicle, and compound 6+vehicle.

FIG. 11 is a graph representing mean discrimination ratios of 9-month-old Ts65Dn mice and control mice that were administered with nothing, vehicle, and compound 7+vehicle.

DETAILED DESCRIPTION

Down syndrome (DS), also known as trisomy 21, is a major cause of mental retardation that affects the welfare of more than 400,000 individuals and their families in the United States and millions worldwide, affecting approximately 1 in every 700 births. This syndrome alone is estimated to cost American society $800 million per year, with a $4.5 billion lifetime direct and indirect costs per cohort at a 2% discount rate. The identification and development of treatments for cognitive limitations in patients with DS has been hindered by a lack of interest by the pharmaceutical industry and a lack of comprehensive understanding of existing animal models. At present, the pharmaceutical industry has failed to find compounds that may improve cognitive performance without increasing the inherent risk of seizures in the DS patient population. One tool in the search for a medicament that may alleviate cognitive deficiencies associated with DS is the genetically modified Ts65Dn mouse.

The Ts65Dn mouse is trisomic for a segment of mouse chromosome 16 that contains many of the gene homologs located on human chromosome 21 and displays many of the phenotypes of DS patients including memory deficits on tasks that are dependent on hippocampal function. This phenotype is hypothesized by many to result, in part, as a consequence of aberrantly enhanced inhibitory neurotransmission. In the vast majority of cases, synaptic plasticity in Ts65Dn mice has not been examined using the physiological induction stimuli that are relevant to the rhythms correlated with learning and memory.

Despite the general lack of DS treatments, pentylenetetrazol (PTZ), a potent γ-aminobutyric acid (GABA) receptor antagonist and a compound with serious human seizure liability, has aroused interest for use in clinical trials based on limited animal testing. Other therapeutic compounds that improve cognitive function in a limited number of tasks in Ts65Dn mice have not been systematically evaluated for enhanced seizure liability; it is now thought that the increased incidence of epilepsy in DS and audiogenic seizures in the Ts65Dn mouse makes the mouse an ideal testing ground for a drug discovery effort considering patient safety.

Several studies have been leveled at the GABA inhibitory pathways in hopes of being able to improve cognition. GABA is a neurotransmitter that is the principal inhibitory transmitter in the mammalian central nerve system (CNS). PTZ is used to antagonize GABA receptors, thus lowering the amount of GABA released and thereby limiting the amount of inhibitory signals produced. Studies that have employed GABA antagonists have generally shown an improvement in cognition of study subjects. The clinical development of certain GABA antagonists was prevented due to the anxiogenic effects and concerns of seizures observed in studies that were conducted.

Patients with DS have an increased incidence of epilepsy in childhood, but as patients age, the incidence of seizures rises to approximately 26% of the population. While the Ts65Dn mouse has audiogenic seizures and epileptic extensor spasms following administration of a $GABA_B$ receptor agonist, additional seizure susceptibility tests have not been performed. Given the propensity of DS patients to have epilepsy, seizure thresholds in this DS model should be determined. In addition, compounds that reduce inhibitory signals and improve cognitive performance in these mice may reduce seizure thresholds. $5-HT_6$ receptor antagonists may positively affect long term potentiation (LTP) by decreasing the excitability of GABAergic interneurons. A $5-HT_6$ receptor antagonist may enhance cognition without increasing seizure liability since $5-HT_6$ receptor antagonists have been shown to be well tolerated and may even be paradoxically anticonvulsant. A battery of acute seizure models may be used to determine if putative treatments enhance seizure liability in Ts65Dn mice. These models are rapid to use, sensitive to subtle changes in seizure threshold, standard in drug discovery, and mice can be used multiple times.

Several different types of GABA receptors exist. Depending on the ailment, one of the 5 GABA alpha receptors may be able to attenuate a particular ailment, one of which is Down syndrome. Studies have been performed on Ts65Dn mice to see if Down syndrome's common phenotypes of low cognition could be alleviated with a GABA antagonist. The studies concluded that the Ts65Dn mice indeed have increased cognition, but the exact mechanism or receptor to which the observed cognition improvement can be attributed is not known.

Another group of neurotransmitter receptors that have received attention in recent years are the serotonin receptors. Codony et al. (2010) *Int. Rev. Neurobiol.* 94, 89-110. The lack of serotonin, also known as 5-hydroxytryptamine (5-HT), has been linked to a number of neurological disorders, such as depression. Like the aforementioned GABA receptor classes, there is a variety of 5-HT receptor subtypes, 15 identified thus far and grouped into seven different classes. Each of the receptors may play a unique role in a number of different neurological ailments. For example, $5-HT_6$ receptor antagonists have found some success in the treatment of Alzheimer's disease (AD) and other diseases that are brought upon through age, trauma, or infection. Members of this class have also failed in some clinical trials designed to address their potential as treatment for AD. These failures shed doubt on the use of these compounds as a class in the treatment of AD.

In addition, there are fundamental genetic differences between an individual with trisomy 21 to non-trisomic people as well as fundamental anatomical and cognitive differences between people with DS and AD. Most evident is that DS is due to a specific genetic anomaly, comprising a third copy of the genetic contents of chromosome 21 (compared to two in the non-DS population) whereas AD is a neurodegenerative disease of largely unknown cause except for the less than 5% of cases caused by variations in one of about 6 genes. In addition, the overall brain morphology of the person with DS is different in many aspects, two of which are the smaller size of many parts of the DS brain and fewer neuronal cells in general. Using positron emission tomography (PET), researchers have shown that the neurophysiology of an aging DS brain differs from that of an AD brain that does not have DS. Specifically, the PET imaging showed higher levels of probe binding in at least two regions of the DS brain relative to the AD brain. Nelson et al. (2012) *Prog. Brain. Res.* 197, 101-121. Furthermore, DS is a condition present at birth whereas AD is a disease of aging. Finally, DS cognitive defects do not progress in contrast with those associated with AD which typically progress throughout the 6-15 years prior to demise.

Humans with DS and Ts65Dn mice both show an increase in the expression of amyloid precursor protein (APP), a protein that is thought to be one of the main contributors to the neuronal plaques that form in AD patients. However, these plaques have not been found in Ts65Dn mice. A number of drugs that prevent the production of APP have been shown to alleviate cognition and memory imbalances in Ts65Dn mice. However, the mechanism through which $5-HT_6$ receptor antagonists alleviate symptoms is unclear due to the plethora of downfield neuronal pathways that the drug could affect.

In addition to elevated APP protein in Ts65Dn mice, this mouse model also appears to possess an enhanced GABAergic interneuron inhibitory network. The latter may explain why GABA receptor antagonists have successfully alleviated cognitive deficiencies in humans and mice that are trisomic for the relevant chromosome. However, the exact mechanism of action of $5-HT_6$ receptor antagonists is not known as there are many neurological pathways that these compounds could modulate to produce this effect.

This concept is exemplified with dimebolin, a molecule that was prescribed in Russia as a non-selective anti-histamine for allergies, but which has since been used as a $5-HT_6$ receptor antagonist in studies designed to investigate its impact on cognitive recovery of AD patients. Aside from working on histaminergic and $5-HT_6$ receptors, dimebolin has also been discovered to act in a plethora of other ways, such as an acetylcholinesterase inhibitor, an N-methyl-D-aspartate receptor antagonist, an inhibitor of voltage-gated calcium channels, and a modulator of mitochondrial transition pore. Furthermore, dimebolin has been found to inhibit 18 other receptors by 50% at a concentration of 10 μM. Though dimebolin is a $5-HT_6$ receptor antagonist, it is approximately 20 times weaker in its ability to bind. Thus, its various properties of cognitive enhancement could come from any one of its pharmacological effects on its various targets.

In summary, because neither the DS genotype nor phenotype is the same as that of AD, one of skill in the art would not find it obvious that their respective cognitive deficits could be rescued by the same class of compounds. Consequently, the methods we disclose to use $5-HT_6$ receptor antagonists to alleviate the cognitive deficits associated with DS are both surprising and distinct from those that propose to use specific subsets of $5-HT_6$ receptor antagonists to enhance or retard the progression of cognitive decline in conditions such as schizophrenia and AD.

Through the use of a mouse model of DS, the Ts65Dn mouse, we disclose evidence herein that $5-HT_6$ receptor antagonists may alleviate the cognitive deficits observed in human subjects suffering from DS. Species within the claimed genus of 5-HT$_6$ receptor antagonists restored the cognitive function of Ts65Dn mice almost to the level of control mice as demonstrated by an improved ability to differentiate between a familiar object in a familiar location and a novel object in a novel location. Unlike the aforementioned compound PTZ, 5-HT$_6$ receptor antagonists were well tolerated by human subjects in various clinical trials designed to test their effectiveness to treat AD. Additionally, these compounds may even be paradoxically anti-convulsant. While members of this class of compounds may also modulate receptors other than the 5-HT$_6$ receptor, they have the highest affinity for the 5-HT$_6$ receptor. In support of the hypothesis that members of the claimed class of compounds improve the cognitive deficits associated with DS by modulating the 5-HT$_6$ receptor, compound 5, which binds the human but not the mouse 5-HT$_6$ receptor, did not alter the cognitive abilities of the Ts65Dn mouse. Consequently, the data disclosed herein support the claimed use of 5-HT$_6$ receptor antagonists for the treatment of cognitive deficits associated with DS.

The present disclosure provides compounds, compositions, and methods of administration that may improve the cognitive capacity of people with intellectual disabilities, an IQ of less than 85, diagnosed with mental retardation, and, most specifically, those with DS.

I. Definitions

Unless specifically defined otherwise, the technical terms, as used herein, have their normal meaning as understood in the art. The following explanations are provided to better describe the present compounds, compositions, and methods, and to guide those of ordinary skill in the art in the practice of the present disclosure. It is also to be understood that the terminology used in the disclosure is for the purpose of describing particular embodiments and examples only and is not intended to be limiting.

Unless otherwise specified, the nomenclature used herein generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Advanced Chemistry Development, Inc., Toronto, Canada.

As used herein, the term "control mice" is meant to refer to mice of the same genetic background as Ts65Dn mice but which lack the trisomy of chromosome 16.

As used herein, the term "alk" or "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In some embodiments, an alkyl group can contain from 1 to about 20 carbon atoms. "Lower alk" refers to either lower alkyl or lower alkenyl species, having from 1 to about 4 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents, such as F, Cl, Br, I, or At. Example haloalkyl groups include —CF$_3$, —CHF$_2$, —CCl$_3$, —CHCl$_2$, —CCl$_5$, —C$_2$F$_5$, —CH$_2$CF$_2$CH$_2$F, —CH$_2$CF$_2$CHF$_2$, —CH$_2$CF$_2$CF$_3$, and the like. An alkyl group in which all of the hydrogen atoms are replaced with halogen atoms can also be referred to as "perhaloalkyl."

As used herein, "alkylene" or "alkylenyl" refers to a bivalent alkyl group. An example alkylene group is methylene or ethylene.

As used herein, "alkenylene" or "alkenylenyl" refers to a bivalent alkenyl group.

As used herein, "competitive antagonist" means a receptor antagonist that binds to, but does not activate, the receptor. The competitive antagonist competes with available agonists, including the receptor's endogenous ligand, for receptor binding sites.

As used herein, "cholinesterase inhibitor" means a biologically active compound that inhibits the activity of or inactivates the biological action of acetylcholinesterase.

As used herein, "acetylcholine receptor antagonist" means a compound that directly inhibits activity of the acetylcholine receptor by acetylcholine or another acetylcholine receptor agonist.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic (e.g., having 2, 3 or 4 fused rings) or spirocyclic. Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. Carbocyclyl groups can be aromatic (e.g., "aryl") or non-aromatic (e.g., "cycloalkyl"). In some embodiments, carbocyclyl groups can have from about 3 to about 30 carbon atoms, about 3 to about 20, about 3 to about 10, or about 3 to about 7 carbon atoms.

As used herein, "aryl" refers to an aromatic carbocyclyl group including monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocyclyl groups including cyclized alkyl, alkenyl, and alkynyl groups. Cycloalkyl groups can include bi- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like.

As used herein, "heterocyclyl" or "heterocycle" refers to a saturated or unsaturated carbocyclyl group wherein one or more of the ring-forming carbon atoms of the carbocyclyl group are replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can be characterized as having 3-14 ring-forming atoms. In some embodiments, heterocyclyl groups can contain, in addition to at least one heteroatom, from about 1 to about 20, about 2 to about 10, or about 2 to about 7 carbon atoms and can be attached through a carbon atom or heteroatom. In further embodiments, the heteroatom can be oxidized (e.g., have an oxo or sulfindo substituent) or a nitrogen atom can be quaternized. Examples of heterocyclyl groups include morpholino, and thiomorpholino. Also included are fused ring and spiro compounds containing, for example, the above heterocycles.

As used herein, "heteroaryl" groups are aromatic heterocyclyl groups and include monocyclic and polycyclic (e.g., having 2, 3 or 4 fused rings) aromatic hydrocarbons that have at least one heteroatom ring member such as sulfur, oxygen, or nitrogen. Examples of heteroaryl groups include pyridyl and pyrimidinyl. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocyclyl groups including cyclized alkyl, alkenyl, and alkynyl groups where one or more of the ring-forming carbon atoms is replaced by a heteroatom such as an O, N, or S atom. Example heterocycloalkyl groups include morpholino, thiomorpholino, piperazinyl, and the like. Also included in the definition of heterocycloalkyl are multiple cyclic systems, such as octahydropyrrolo[1,2-A]pyrazine or octayhydropyrido[1,2-A]pyrazine, and moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "aryloxy" refers to an —O-aryl group. An example aryloxy group is phenoxy.

As used here, "haloalkoxy" refers to an —O-haloalkyl group. An example haloalkoxy group is —OCF$_3$.

As used herein, "carbocyclylalkyl" refers to an alkyl moiety substituted by a carbocyclyl group. Example carbocyclylalkyl groups include "aralkyl" (alkyl substituted by aryl ("arylalkyl")) and "cycloalkylalkyl" (alkyl substituted by cycloalkyl). Example aralkyl groups include "benzyl" (C$_6$H$_5$CH$_2$—). In some embodiments, carbocyclylalkyl groups have from 4 to 24 carbon atoms.

As used herein, "heterocyclylalkyl" refers to an alkyl moiety substituted by a heterocarbocyclyl group. Example heterocarbocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein, "amino" refers to an —NH$_2$ group. "Alkylamino" refers to an amino group substituted by an alkyl group and "dialkylamino" refers to an amino group substituted by two alkyl groups.

As used herein, "aminocarbonyl" refers to —CONH$_2$.

As used herein, "alkylaminocarbonyl" refers to —CONH (alkyl).

As used herein, "alkylaminocarbonyl" refers to —CON (alkyl)$_2$.

As used herein, "carboxy" or "carboxyl" refers to —COOH.

As used herein, "carboxy alkyl ester" refers to —COO-alkyl.

As used herein, "carboxy aryl ester" refers to —COO-aryl.

As used herein, "hydroxy" refers to —OH.
As used herein, "mercapto" refers to —SH.
As used herein, "sulfinyl" refers to —SO.
As used herein, "sulfonyl" refers to —SO$_2$.
As used herein, "aminosulfonyl" refers to —SO$_2$NH$_2$.
As used herein, "alkylaminosulfonyl" refers to —SO$_2$NH (alkyl).
As used herein, "dialkylaminosulfonyl" refers to —SO$_2$N (alkyl)$_2$.
As used herein, "arylsulfonyl" refers to —SO$_2$-aryl.
As used herein, "arylsulfinyl" refers to —SO-aryl.
As used herein, "alkylsulfonyl" refers to —SO$_2$-alkyl.
As used herein, "alkylsulfinyl" refers to —SO-alkyl.

As used herein, "combinations thereof" is meant to refer to concatenation of two or more moieties recited for a given variable. For example, "—CH$_2$, —NH, —CO, and combinations thereof" would include —CH$_2$NH, —CH$_2$CO, —CONH, —CH$_2$NHCO, and other stable combinations.

As used herein, "child" refers to a human under the age of 20 years.

As used herein, "inverse agonist" refers to a compound that binds to the same receptor as an agonist of that receptor but which induces a response that is opposite of that agonist.

As used herein, "inhibitor" refers to a ligand which binds to a receptor in any way and which blocks or dampens the agonist-mediated response.

"Metal" refers to any metal that could be cationic, i.e. monovalent or multivalent. For example, the metal may be monovalent sodium or potassium, divalent zinc, or a metal known to have several oxidation states, such as $V^+$, $V^{2+}$, $V^{3+}$, $V^{4+}$, $V^{5+}$, or even $V^-$ with the appropriate supporting ligand architecture.

As used herein, "small molecule" means an organic compound having a molecular weight of less than 2,000 Daltons that has a biological effect.

II. Compounds

In one embodiment, the relevant class of compounds are those whose action relates to the binding or modification of structure or function of the 5-HT$_6$ receptor (i.e., 5-HT$_6$ receptor antagonists), which elicit a pharmaceutical effect in which cognitive impairment in DS patients is partially or completely restored, or which an alleviation of psychosis, or where amelioration of a particular disorder is obtained. The present disclosure comprises the use of 5-HT$_6$ antagonists according to Formulae I and II and pharmaceutically acceptable salts thereof, and other compounds known to function as 5-HT$_6$ antagonists. The 5-HT$_6$ receptor antagonists to be used in the methods disclosed include, but are not limited to, compound 1, compound 2, compound 3, compound 4, compound 5, compound 6, and compound 7.

For compounds having a structure according to Formula I:

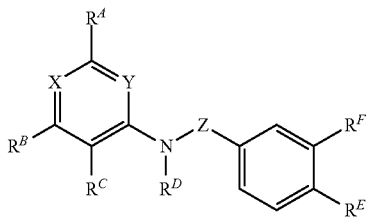

Formula I $R^A$ is selected from —H, —$NH_2$, —NH(alkyl), —N(alkyl)$_2$, —NH(aryl), —N(aryl)$_2$, —N(aryl)(alkyl), —N-heterocycle, or —N-heterocycloalkyl, where, in the case of —N(alkyl)$_2$ or —N(aryl)2, the alkyl groups or the aryl groups can be identical or different;

$R^B$ is selected from —H, —$NH_2$, —NH(alkyl), —N(alkyl)$_2$, —NH(aryl), —N(aryl)$_2$, —N(aryl)(alkyl), —N-heterocycle, or —N-heterocycloalkyl, where, in the case of —N(alkyl)$_2$ or —N(aryl)2, the alkyl groups or the aryl groups can be identical or different;

$R^C$ is selected from —H, —OH, —O(alkyl), —O(aryl), -halogen, -alkyl, or haloalkyl;

$R^D$ is selected from —H, -alkyl, -halogen, -haloalkyl, or aryl;

$R^E$ is selected from —H, -halogen, —OH, —O(alkyl), —$NH_2$, —NH(alkyl), or —N(alkyl)$_2$, where, in the case of —N(alkyl)$_2$, the alkyl groups can be identical or the alkyl groups can be different length alkyl chains;

$R^F$ is —H, —$NH_2$, —NH(alkyl), —N(alkyl)$_2$, —NH(aryl), —N(aryl)$_2$, —N(aryl)(alkyl), —N-heterocycle, or —N-heterocycloalkyl, where, in the case of —N(alkyl)$_2$, or —N(aryl)$_2$, the alkyl groups or the aryl groups can be identical or different;

X and Y are independently —N— or —C(H)—; and

Z is selected from —$CH_2$—, —CHX—, —$CX_2$—, —CH(alkyl)-, —CH(aryl)-, —C(aryl)(alkyl)-, —C(alkyl)$_2$-, —C(aryl)$_2$-, —O—, —S—, —S(=O)—, or —S(=O)$_2$—, where X is a halogen and where, in the case of —C(alkyl)$_2$-, or —C(aryl)$_2$-, the alkyl groups or the aryl groups can be identical or different;

Exemplary compounds according to Formula I include, for example:

Compound 1, also known as N-(3,5-dichloro-2-methoxyphenyl)-4-methoxy-3-(piperazin-1-yl)benzenesulfonamide, Compound 1

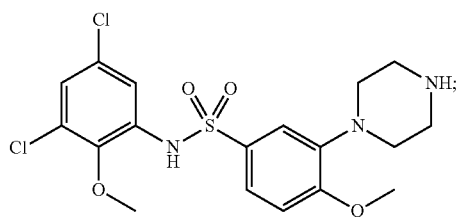

and

Compound 5, also known as 4-amino-N-(2,6-bis(methylamino)pyrimidin-4-yl)benzenesulfonamide, Compound 5

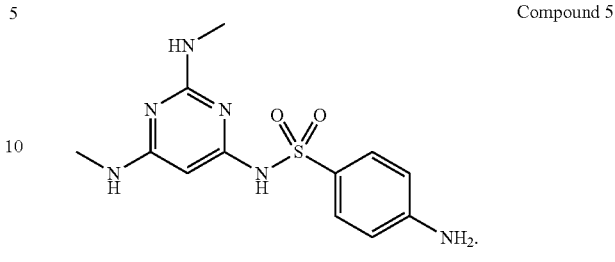

For compounds having a structure according to Formula II:

Formula II

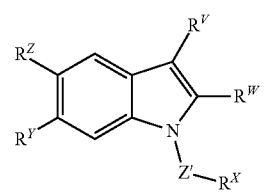

$R^Z$ is selected from —H, —OH, —O(alkyl), —O(aryl)-O—S-phenyl, —O—S(=O)-phenyl, —O—S(=O)$_2$-phenyl, —O—S-alkyl, —O—S(=O)-alkyl, —O—S(=O)$_2$-alkyl, —O—S-haloalkyl, —O—S(=O)-haloalkyl, —O—S(=O)$_2$-haloalkyl, —O—S-2,6-dihalophenyl, —O—S(=O)-2,6-dihalophenyl, or —OS(=O)$_2$-2,6-dihalophenyl;

$R^Y$ is selected from —H, -halogen, —$NH_2$, —NH(alkyl), —N(alkyl)$_2$, —NH(aryl), —N(aryl)$_2$, —N(aryl)(alkyl), —N-heterocycle, or —N-heterocycloalkyl, where, in the case of —N(alkyl)$_2$, or —N(aryl)$_2$, the alkyl groups or the aryl groups can independently be identical or different;

$R^W$ is selected from —H, —OH, —O(alkyl), —O(aryl), -halogen, -alkyl, or haloalkyl;

$R^V$ is selected from —H, -2-ethyl-NH(alkyl), -2-ethyl-N(alkyl)$_2$, -2-ethyl-NH(aryl), -2-ethyl-NH(arylalkyl), -2-ethyl-NH(benzyl), -2-ethyl-NH(alkoxybenzyl), -2-ethyl-NH(haloalkoxybenzyl), -2-ethyl-NH(m-haloalkoxybenzyl), -2-ethyl-N(aryl)$_2$, -2-ethyl-N(alkyl)(aryl), -3-propyl-NH(alkyl), -3-propyl-N(alkyl)$_2$, -3-propyl-NH(aryl), -3-propyl-N(aryl)$_2$, -3-propyl-N(aryl)(alkyl), —N-heterocycle, or —N-heterocycloalkyl, where, in the case of a dialkyl or diaryl nitrogen, the alkyl groups or the aryl groups can be identical or different;

Z' is selected from —H, —$CH_2$—, —CHX—, —$CX_2$—, —CH(alkyl)-, —CH(aryl), —C(aryl)(alkyl)-, —C(alkyl)$_2$-, —C(aryl)$_2$-, —O—, —S—, —S(=O)—, or —S(=O)$_2$—, where X is a halogen and where, in the case of —C(alkyl)$_2$- or —C(aryl)$_2$-, the alkyl groups or the aryl groups can be identical or different;

$R^X$ is optionally present, and if present is selected from —H, —OH, —O(alkyl), —O(aryl), -halogen, -alkyl, -haloalkyl, or -aryl.

Exemplary compounds according to Formula II include, for example:

Compound 2, also known as 2-(5-methoxy-2-phenyl-1H-indol-3-yl)-N,N-dimethylethanamine, Compound 2

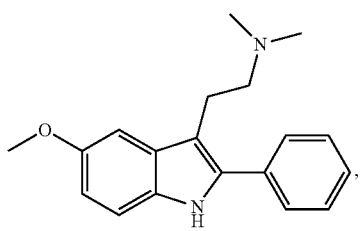

Compound 3, also known as 2-(1-(naphthalen-1-ylsulfonyl)-1H-indol-6-yl)octahydropyrrolo[1,2-a]pyrazine, Compound 3

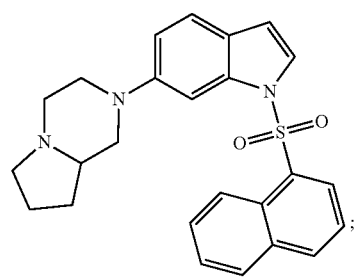

Compound 4, also known as 1-methyl-3-(1-methylpiperidin-4-yl)-1H-indol-5-yl 2,6-difluorobenzenesulfonate, Compound 4

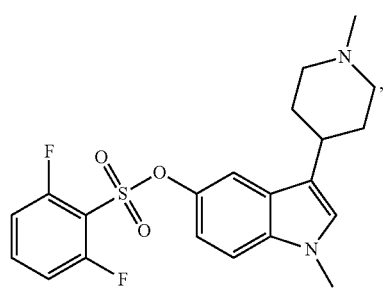

and

Compound 6, also known as 2-(6-fluoro-1H-indol-3-yl)-N-(3-(2,2,3,3-tetrafluoropropoxyl)benzyl)ethanamine, Compound 6

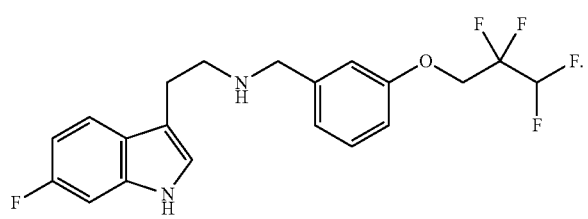

Another exemplary compound that can be used in the methods disclosed herein is Compound 7, also known as 3-(phenylsulfonyl)-8-(piperazin-1-yl)quinoline, Compound 7

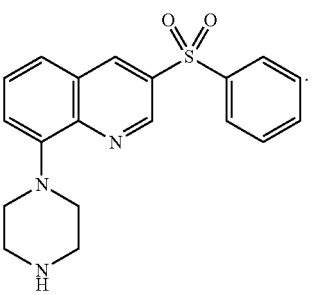

Accordingly, 5-$HT_6$ receptor antagonists are used in the methods disclosed herein. The 5-$HT_6$ receptor antagonists may include, but are not limited to, exemplary compounds 1-7. In one embodiment, the 5-$HT_6$ receptor antagonists as used for the methods described herein comprise small molecule 5-$HT_6$ receptor antagonists as defined herein. In one embodiment, the small molecule 5-$HT_6$ receptor antagonists have a molecular weight that is less than 2,000 Daltons. In another embodiment, the small molecule 5-$HT_6$ receptor antagonists have a molecular weight that is less than 1,000 Daltons. In yet another embodiment, the small molecule 5-$HT_6$ receptor antagonists have a molecular weight that is less than 800 Daltons.

In some embodiments, the 5-$HT_6$ receptor antagonists as used for the methods described herein comprise compounds that directly bind the 5-$HT_6$ receptor. In other embodiments, the 5-$HT_6$ receptor antagonists as used for the methods described herein comprise competitive antagonists of the 5-$HT_6$ receptor as defined herein. In still other embodiments, the 5-$HT_6$ receptor antagonists as used for the methods described herein comprise inverse agonists of the 5-$HT_6$ receptor as defined herein.

These 5-$HT_6$ receptor antagonists have been found to have a surprising effect on the rescue of cognition in Ts65Dn mice. Ts65Dn mice are genetically modified mice that have phenotypes that mimic human Trisomy 21, i.e., DS. The Ts65Dn line of mice has proven to be an effective model for drug testing.

Compounds 1-4 have been found to restore the cognition of Ts65Dn mice to nearly that of non-Ts65Dn (control) mice. The main receptor/neural pathway on which these compounds are thought to be acting is the 5-$HT_6$ receptor, of which compounds 1-7 are antagonists. While compound 5 is a 5-$HT_6$ receptor antagonist, it does not bind to the mouse 5-$HT_6$ receptor and, consequently, does not restore cognition of Ts65Dn mice. Compound 5, thus acts as a negative control and supports the interpretation that the disclosed compounds act to restore cognition by antagonizing the 5-$HT_6$ receptor.

Compounds 1-7 are to be used to improve cognition in human patients who are afflicted with DS, also known as Trisomy 21. Other human patients that these compounds could be used to treat are those with intellectual disabilities, those with an IQ of less than 85, those diagnosed with mental retardation, those with DS and its comorbid disorders (Autism spectrum disorders, depression, anxiety, mild psychosis, attention deficit hyperactivity disorder (ADHD), and obsessive compulsive disorder (OCD), and disorders involving speech and language), Fragile X syndrome, velocardiofacial syndrome and associated comorbidities, fetal alcohol syndrome, brain trauma, and cerebral palsy.

Compound 1 is a piperazinylbenzenesulfonamide 5-$HT_6$ receptor antagonist that has been shown to be a "potent, selective, brain penetrant, orally active 5-HT$_6$ receptor antagonist," and "has a high affinity for human recombinant and native 5-HT$_6$ receptors and is a potent competitive antagonist." Hirst et al. (2006) *Eur. J. Pharmacol.* 553, 109-19.

Compound 2 is a tryptamine analog of 5-HT$_6$ receptor antagonists. It has been shown to reverse scopolamine-induced memory deficits. Mitchell and Neumaier (2008) *Pharmacol. Biochem. Behav.* 88, 291-98.

Compound 3, also known as NPS ALX Compound 4a dihydrochloride is also known to be a 5-HT$_6$ receptor antagonist. Isaac et al. (2000) *Bioorg. Med. Chem. Lett.* 10, 1719-21.

Compound 4, also known as SGS 518 oxalate, which is a highly selective 5-HT$_6$ receptor antagonist created through a medicinal chemistry approach. Romero et al. (2006) *Br. J. Pharmocol.* 148, 1133-43.

Compound 5, also known as Ro 04-6790, is known to behave as a competitive 5-HT$_6$ receptor antagonist. Sleight et al. (1998) *Br. J. Pharmacol.* 124, 556-62.

Compound 6, also known as Lu-AE-58054, is a potent 5-HT6 receptor antagonist shown to have no agonist activity. Arnt et al. (2010) *Int. J. Neuropsychopharmacol.* 13, 2021-33.

Compound 7, also known as SB-742457, is a candidate therapy for AD and schizophrenia. Liu and Robichaud (2009) *Drug. Dev. Res.* 70, 145-68.

It is further appreciated that certain features of the disclosure, which are, for clarity, described in the context of separate embodiments, can also be provided in combination in a single embodiment. Conversely, various features of the invention that are, for brevity, described in the context of a single embodiment, can also be provided separately or in any suitable subcombination.

III. Pharmaceutical Compositions

Examples of pharmaceutically acceptable acid addition salts for use with the compounds disclosed include those derived from mineral acids, such as hydrochloric, hydrobromic, phosphoric, metaphosphoric, nitric, and sulfuric acids, and organic acids, such as tartaric, acetic, citric, malic, lactic, fumaric, benzoic, glycolic, gluconic, succinic, p-toluenesulphonic, and arylsulphonic acids, for example. Examples of pharmaceutically acceptable base addition salts for use with the compounds disclosed include those derived from non-toxic metals such as sodium or potassium, ammonium salts, and organoamino salts such as triethylamine salts. Numerous appropriate such salts will be known to those of ordinary skill.

The neutral forms of the compounds disclosed may be regenerated by contacting a salt of the compound with a base or acid and isolating the parent compound in the conventional manner. The parent form of the compound differs from the various salt forms in certain physical properties, such as solubility in polar solvents, but otherwise the salts are equivalent to the parent form of the compound.

The compounds disclosed can also include all isotopes of atoms occurring in the intermediates or final compounds. Isotopes include those atoms having the same atomic number but different mass numbers. For example, isotopes of hydrogen include tritium and deuterium.

Some of the compounds disclosed can exist in unsolvated forms as well as solvated forms, including hydrated forms. In general, the solvated forms are equivalent to unsolvated forms and are intended to be encompassed within the scope of the present disclosure. Certain compounds may exist in multiple crystalline or amorphous forms. In general, all physical forms are equivalent for the uses contemplated by the present disclosure and are intended to be within the scope of the present disclosure.

In addition to salt forms, the present disclosure provides compounds that may be in a prodrug form. Prodrugs of the compounds described herein are those compounds that readily undergo chemical changes under physiological conditions to provide the compounds of the present disclosure. Additionally, prodrugs can be converted to the compounds of the present invention by chemical or biochemical methods in an ex vivo environment. For example, prodrugs can be slowly converted to the compounds of the present disclosure when placed in a transdermal patch reservoir with a suitable enzyme or chemical reagent.

Prodrugs of the disclosed compounds may be prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. For example, a prodrug may be a lower alkyl phosphonate ester, such as a methyleno phosphonate ester or an isopropyl phosphonate ester.

In order to use a compound of Formulae (I) or (II), or compound 7, or a pharmaceutically acceptable salt or complex thereof for the treatment of humans and other mammals, it is normally formulated in accordance with standard pharmaceutical practice as a pharmaceutical composition.

The compounds can be administered by different routes including intravenous, intraperitoneal, subcutaneous, intramuscular, oral, topical (transdermal), or transmucosal administration. For systemic administration, oral administration may be used. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. The 5-HT$_6$ antagonists may also be administered by intraventricular or intrathecal injection. For injection, the compounds are formulated in liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be achieved by transmucosal or transdermal methods. For transmucosal or transdermal administration, penetrants appropriate to the barrier to be permeated may be used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds can be formulated into ointments, salves, gels, or creams, as is generally known in the art.

In order to use a compound of the invention, or a pharmaceutically acceptable salt thereof, for the therapeutic treatment of a warm-blooded animal, such as humans, said ingredient is normally formulated in accordance with standard pharmaceutical practice as a pharmaceutical composition.

Therefore in another aspect the present invention provides a pharmaceutical composition that comprises a 5-$HT_6$ receptor antagonist, such as compounds 1, 2, 3, 4, 5, 6, or 7 or a pharmaceutically acceptable salt thereof (active ingredient), and a pharmaceutically acceptable adjuvant, excipient, diluent, or carrier. In a further aspect the present invention provides a process for the preparation of said composition that comprises mixing an active ingredient with a pharmaceutically acceptable adjuvant, diluent, or carrier. Depending on the mode of administration, the pharmaceutical composition will, for example, comprise from 0.05% to 99% w (percent by weight), such as from 0.05% to 80% w, for example, from 0.10% to 70% w, such as from 0.10% to 50% w, of active ingredient, all percentages by weight being based on total composition.

The pharmaceutical compositions of this invention may be administered in a standard manner for the disease condition that it is desired to treat, for example by topical (such as to the lung and/or airways or to the skin), oral, rectal, or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops, or sterile injectable aqueous or oily solutions or suspensions.

A suitable pharmaceutical composition of this invention is one suitable for oral administration in unit dosage form, for example a tablet or capsule that contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous, or intramuscular dose of 0.01 mg/kg to 100 mg/kg of compound, for example in the range of 0.1 mg/kg to 20 mg/kg or from 3 mg/kg to 10 mg/kg, the composition being administered 1 to 4 times per day. The intravenous, subcutaneous, or intramuscular dose may be given by means of a bolus injection. Alternatively, the intravenous dose may be given by continuous infusion over a period of time. Alternatively, each patient will receive a daily oral dose that is approximately equivalent to the daily parenteral dose, the composition being administered 1 to 4 times per day.

This disclosure further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

An example of a combination therapy includes administering at least one 5-$HT_6$ receptor antagonists and a cholinesterase inhibitor. Examples of cholinesterase inhibitors include physostigmine, galantamine, pyridostigmine, and neostigmine. For example, at least one of the 5-$HT_6$ receptor antagonists as disclosed herein may be administered with a cholinesterase inhibitor. The combination therapy may comprise a 5-$HT_6$ receptor antagonist that is a small molecule administered with a cholinesterase inhibitor. Alternatively, the combination therapy may comprise a 5-$HT_6$ antagonist that is a competitive 5-$HT_6$ receptor antagonist administered with a cholinesterase inhibitor. In another embodiment, the combination therapy may comprise a 5-$HT_6$ antagonist that is an inverse 5-$HT_6$ receptor agonist administered with a cholinesterase inhibitor.

A second example of a combination therapy includes administering at least one 5-$HT_6$ receptor antagonists and an acetylcholine receptor agonist. An example of an acetylcholine receptor antagonist is carbachol. For example, at least one of the 5-$HT_6$ receptor antagonists as disclosed herein may be administered with an acetylcholine receptor agonist. The combination therapy may comprise a 5-$HT_6$ receptor antagonist that is a small molecule administered with an acetylcholine receptor agonist. Alternatively, the combination therapy may comprise a 5-$HT_6$ antagonist that is a competitive 5-$HT_6$ receptor antagonist administered with an acetylcholine receptor agonist. In another embodiment, the combination therapy may comprise a 5-$HT_6$ antagonist that is an inverse 5-$HT_6$ receptor agonist administered with an acetylcholine receptor agonist.

The amounts of various cognitive enhancement compounds to be administered can be determined by standard procedures taking into account factors such as the compound's $IC_{50}$ value, $EC_{50}$ value, or $OC_{50}$ value; the biological half-life of the compound; the age, size, and weight of the patient; and the disease or disorder associated with the patient. The significance of these and other factors to be considered are known to those of ordinary skill in the art.

Amounts administered also depend on the routes of administration and the degree of oral bioavailability. For example, for compounds with low oral bioavailability, relatively higher doses may have to be administered.

The composition may be in unit dosage form. For oral application, for example, a tablet or capsule may be administered; for nasal application, a metered aerosol dose may be administered; for transdermal application, a topical formulation or patch may be administered; and for transmucosal delivery, a buccal patch may be administered. In each case, dosing is such that the patient may administer a single dose.

Each dosage unit for oral administration contains suitably from 0.01 to 500 mg/kg, such as from 0.1 to 50 mg/kg, of a compound of Formulae (I), (II), or a pharmaceutically acceptable salt or complex thereof, calculated as the free base. The daily dosage for parenteral, nasal, oral inhalation, transmucosal, or transdermal routes contains suitably from 0.01 mg/kg to 100 mg/kg of a compound of Formulae (I) or (II). A topical formulation contains suitably 0.01% to 5.0% of a compound of Formulae (I) or (II). The active ingredient may be administered as a single dose or in multiple doses, for example, from 2 to 6 times per day, sufficient to exhibit the desired activity, as is readily apparent to one skilled in the art.

The physician or other health care professional can select the appropriate dose and treatment regimen based on the subject's weight, age, and physical condition. Dosages will generally be selected to maintain a serum level of compounds of the invention between about 0.01 µg/cc and about 1000 µg/cc, preferably between about 0.1 µg/cc and about 100 µg/cc. For parenteral administration, an alternative measure of an exemplary amount is from about 0.001 mg/kg to about 10 mg/kg (alternatively, from about 0.01 mg/kg to about 10 mg/kg), such as from about 0.01 mg/kg to about 1 mg/kg (from about 0.1 mg/kg to about 1 mg/kg), will be administered. For oral administrations, an alternative measure of administration amount is from about 0.001 mg/kg to about 10 mg/kg (from about 0.1 mg/kg to about 10 mg/kg), such as from about 0.01 mg/kg to about 1 mg/kg (from about 0.1 mg/kg to about 1 mg/kg). For administrations in suppository form, an alternative measure of administration amount is from about 0.1 mg/kg to about 10 mg/kg, such as from about 0.1 mg/kg to about 1 mg/kg.

IV. Methods of Treatment

As used herein, "treatment" of a disease or condition includes, but is not limited to, prevention, retardation, and prophylaxis of the disease, syndrome, or condition.

Diseases and disorders that may be treated include Down syndrome (DS) and its comorbid disorders (Autism spectrum disorders, depression, anxiety, mild psychosis, attention deficit hyperactivity disorder (ADHD), and obsessive compulsive disorder (OCD), and disorders involving speech and language), Fragile X syndrome, velocardiofacial syndrome and associated comorbidities, fetal alcohol syndrome, brain trauma, and cerebral palsy.

In an embodiment, the present compounds are used to increase cognition of a patient with DS, those with intellectual disabilities, those with an IQ of less than 85, or those diagnosed with mental retardation and the conditions listed in the preceding paragraph above, by administering a therapeutically effective amount of compounds of the class of compounds described in section I.

In another embodiment, the present compounds are co-administered with saline administered intravenously, or commonly used adjuvants/excipients that are well known to those skilled in the art when orally consumed.

Without being bound by theory, it is believed that the compounds disclosed bind to the 5-$HT_6$ receptors of the patient, which is believed to be the mechanism of action that increases cognition in patients.

In another embodiment, a method of treating DS includes administering an effective amount of a 5-$HT_6$ receptor antagonist to a subject in need thereof.

In another embodiment, the method comprises administering a 5-$HT_6$ receptor antagonist that is selected from small molecule 5-$HT_6$ receptor antagonists, direct 5-$HT_6$ receptor antagonists, and inverse 5-$HT_6$ receptor agonists Another aspect of the present disclosure includes a method of treating a patient comprising administering to the patient a present compound in an amount of between 0.01 to 100 mg/kg, such as between 3 to 10 mg/kg of an individual.

In various embodiments, the compound or compounds administered to a patient cause an increase in cognition, an alleviation of psychosis, or amelioration of a particular disorder listed herein, having a duration of up to one hour, about one to about twenty-four hours, about one to about twelve hours, about one to about six hours, about one to about five hours, about one to about four hours, about two to about five hours, about two to about four hours, or about three to about six hours as suggested by preclinical studies.

In additional different embodiments, the compound or compounds administered to a patient cause an increase in cognition of up to two-fold, two- to five-fold, five- to ten-fold, and at least 10-fold greater than the basal cognition level in the patient. The basal cognition is measured with respect to a patient not undergoing treatment.

The instant disclosure also includes kits, packages, and multi-container units containing the herein described pharmaceutical compositions, active ingredients, and/or devices and consumables that facilitate the administration the same for use in the prevention and treatment of diseases and other conditions in mammalian subjects.

In an embodiment, the compounds may be formulated in a pharmaceutical preparation for delivery to a subject. The compounds may be contained in a bulk dispensing container or unit or multiunit dosage form. Optional dispensing means can be provided, for example, a pulmonary or intranasal spray applicator. Packaging materials optionally include a label or instruction indicating for what treatment purposes and/or in what manner the pharmaceutical agent packaged therewith can be used.

In an embodiment, the method of treating DS and its comorbid disorders (Autism spectrum disorders, depression, anxiety, mild psychosis, attention deficit hyperactivity disorder (ADHD), and obsessive compulsive disorder (OCD), and disorders involving speech and language), Fragile X syndrome, velocardiofacial syndrome and associated comorbidities, fetal alcohol syndrome, brain trauma, and cerebral palsy, those with intellectual disabilities, those with an IQ of less than 85, or those diagnosed with mental retardation, comprises administering a therapeutically effective amount of a compound provided herein.

The specific examples included herein are for illustrative purposes only and are not to be considered as limiting to this disclosure. Any active agents and reagents used in the following examples are either commercially available or can be prepared according to standard literature procedures by those skilled in the art of organic synthesis. In light of this disclosure, those of skill in the art will recognize that variations of these examples and other examples of the disclosed method would be possible without undue experimentation.

Examples

Ts65Dn/DnJ Mouse Down Syndrome Model

Male Ts65Dn/DnJ mice and male littermates were obtained from a commercial supplier (Jackson Laboratory, Bar Harbor, Me.), and tested at approximately 12-32 weeks of age, at a weight of 25-30 grams. Animals were kept on a 12 hour light/dark cycle and experimentation was conducted during the light portion of the cycle. Animals had unlimited access to food and water. All animals used were housed individually to limit the interference of social interaction on cognitive test performance. Animal care and experimental testing procedures conformed to NIH, IACUC, and AALAC standards and protocols.

The Ts65Dn/DnJ stock, commercially available from Jackson Laboratory, is homozygous for the wild type allele for retinal degeneration. The stock is maintained by repeated backcrossing of Ts65Dn females to B6EiC3H F1 hybrid males derived from a new congenic strain of C3H mice. This new congenic strain (C3Sn.BLiA-Pde6b$^+$) lacks the blindness causing recessive mutant allele. Thus, all trisomic mice purchased were tested without concern for retinal degeneration.

Ts65Dn are compared to their control littermates for the effects of excipients and compounds in altering the performance and rescue of deficits in the Ts65Dn DS mouse model.

The apparatus for these experiments consisted of a 40 cm×40 cm Plexiglas box with clear walls and a dark grey floor. The box was placed on a circular white table 1 m in diameter. Four distinct, approximately 20 cm×20 cm black and white shapes were placed 30 cm away from the midpoint of each side of the box. Objects were made from various washable, non-porous materials (plastic, metal, glass, etc.), 2-7 cm in height and varied in color, pattern and texture. To prevent odor cues, all apparatus and objects were disinfected and deodorized with HDQ after each use.

The experimental paradigms utilized the inherent tendency of rodents to differentially explore novel stimuli over familiar stimuli. Exploration was defined as any investigative behavior where mice have active and direct contact with an object. Such behaviors included head orientation and sniffing within <1.0 cm of the object, pawing, biting, or crawling over the objects. Exploration was recorded with an overhead video camera and the duration of exploration was measured with a stopwatch. The week prior to testing, all animals were handled in daily sessions and given an opportunity to habituate to the clear or red apparatus. Each experimental session presented the animal with new object sets and tests were separated by a minimum 48 hour interval. It should be noted that order effects are not normally observed in exploration tasks. Each test consisted of a Habituation Phase, during which mice display reduced exploration over time as a function of habituation, and a Test Phase on novelty detection that is interpreted to reflect recognition memory.

For each of the 7 compounds 1-7, the compound was administered to Ts65Dn mice via i.p. injection at a concentration of 3.0 mg/kg (compound 1) or 10 mg/kg (compounds 2, 3, 4, 5, 6, and 7) body weight delivered in a vehicle of methyl cellulose+0.2% tween 80 solution, while additional Ts65Dn mice were administered with vehicle alone. Each animal received a volume (ml) of drug in vehicle equal to 1% of its body weight (g) or an equal volume of vehicle alone. Forty minutes after the compound is injected, the Habituation phase begins. Therefore, the Test phase occurs 60 minutes after administration of the drug.

Exploratory Paradigm: Ability to Recognize a Novel Object in a Novel Location

For each experiment the animal was placed in center of the clear acrylic box and presented with two different objects spaced 15 cm apart for 15 minutes of free explorations of the apparatus, stimulus objects, and distal environmental cues (Habituation Phase). After the Habituation Phase, a black container was placed over the mouse for a 5-minute Delay. During this delay, one object was exchanged with a new, unfamiliar object in a novel location (novel object), while the other object is replaced with an identical object in the same location (familiar object). Following the delay the black container was removed, beginning the Test Phase and the mouse is allowed to re-explore for 5 minutes (Test Phase).

The duration of exploration of the Novel and Familiar stimuli during the Test Phase was individually measured with stopwatches, rounding to the 0.5 second. Using these data, the following Discrimination Ratio was calculated: [Exploration of Novel (A)−Exploration of Familiar (B)]/ Total Exploration (A+B). A zero score would reflect no preference for either the novel or familiar object. A positive score reflects a preference for exploration of the novel object, and is associated with the animal's level of hippocampal function and memory or cognition.

The experimental paradigm is shown in FIG. 1. The experiment begins with a 15-minute Habituation Phase during which the animal is free to explore two objects placed 15 cm apart. The animal is then covered with a black box for 5 minutes, during which one of the objects is replaced with an identical object in the same location, while the other object is replaced with a novel object in a novel location. The black box is then removed for the 5-minute Test Phase and the time spent exploring each object is recorded to determine the discrimination ratio.

FIGS. 2 through 11 present the results for experiments demonstrating the ability of compounds belonging to the 5-HT$_6$ receptor antagonist class of compounds to rescue performance of Ts65Dn Down syndrome mice in this hippocampus-dependent cognitive test (Experimental paradigm 1). Error bars represent the standard error of the mean and asterisks indicate significance between groups at the 0.05 level. Significance was determined using a two-tail, paired T-Test.

FIG. 2, shows that the DS mouse model (Ts65Dn) at 3-4 months, cannot discriminate a familiar object from a novel object in a novel location (viz, discrimination ratio; See #0123) whereas a normal littermate can readily perform this task (P<0.001). Therefore, this task was used to assess the ability of 5HT6 receptor antagonists to rescue cognitive deficits.

FIG. 3 shows that treatment with a 5-HT6 receptor antagonist, compound 1 restores the ability of Ts65Dn mice to discriminate a familiar from a novel object placed in a novel location. Treatment with vehicle alone did not increase or decrease mean discrimination ratio for either the Ts65Dn mice or their control littermates. In contrast, treatment of Ts65Dn mice with compound 1+vehicle did result in a significant increase compared to no treatment (P=0.00504) or treatment with vehicle alone (P=0.0169). This increase was not found in control mice who did not respond differently to treatment with compound 1+vehicle vs. vehicle alone.

The data presented in FIG. 4 show that treatment with compound 2 significantly improves cognition (i.e., discrimination ratio) in Ts65Dn mice compared to treatment with vehicle alone (P=0.0114).

In FIG. 5, the data indicate that treatment of Ts65Dn mice with compound 3+vehicle significantly increased cognitive performance (discrimination ratio) compared to treatment with vehicle alone (P=0.0190).

In FIG. 6, the data show that treatment of Ts65Dn mice with compound 4+vehicle resulted in a trend to increased discrimination ratios compared to treatment with vehicle alone (P=0.116), nearly to levels seen in control mice.

FIG. 7 illustrates the specificity of cognitive rescue to 5-HT$_6$ receptor binding. In order to show that the 5HT$_6$ receptor is the target responsible for the cognitive improvements seen in compounds 1-4, a negative control experiment was performed using compound 5 that recognizes the rat but not the mouse 5-HT$_6$ receptor. FIG. 7 shows that treatment of Ts65Dn mice with compound 5, does not improve cognition (i.e., discrimination ratios) compared to vehicle alone, strongly supporting the claim that members of the class of 5-HT$_6$ receptor antagonists rescue cognition in DS (Ts65Dn mouse) model through their binding to and inhibition of 5-HT$_6$ receptor functions.

FIG. 8, illustrates that aging mice with DS (8-month-old Ts65Dn) also respond to compound 1 with an increase in cognitive ability (i.e., discrimination ratio). Without treatment, or in response to vehicle alone, the discrimination ratios for 8-month-old Ts65Dn mice were much lower than for control mice. In contrast, treatment with compound 1 significantly increased discrimination ratios compared both to no treatment (P=0.0337) or to treatment with vehicle alone (P=0.0452). Two weeks after performing these treatment experiments, the Ts65Dn mice were tested to determine whether the effect of the treatment was sustained. The results showed that the treatment effect did not last and mean discrimination ratios had returned to pre-treatment levels. These data indicate that even in aging mice with DS (Ts65Dn), cognitive improvements (i.e., discrimination ratios) resulted from treatment with the 5-HT$_6$ receptor antagonist, compound 1.

FIG. 9 summarizes the rescue of DS (Ts65Dn) cognitive deficits by the class of 5-HT$_6$ receptor antagonists, illustrating the positive responses to treatment with compounds 1-4, and the lack of response to the negative control (compound 5 that does not recognize the mouse 5-HT$_6$ receptor).

In FIG. 10, the data show that that aging mice with DS (9-month-old Ts65Dn) respond to compound 6. Specifically, treatment with vehicle alone did not improve cognitive performance, as the average discrimination ratio was nearly identical to the ratio mice with no treatment. In contrast, treatment with compound 6+vehicle did result in a significant increase in cognitive performance compared to both no treatment (P=0.005) and treatment with vehicle alone (P=0.003).

In FIG. 11, the data show that aging mice (9-month-old Ts65Dn) also respond to compound 7. Specifically, treatment with compound 7+vehicle significantly improves cognitive performance (discrimination ratio) in Ts65Dn mice compared to treatment with vehicle alone (P=0.035).

All publications, including but not limited to patents and patent applications, cited in this specification are herein incorporated by reference as if each individual publication were specifically and individually indicated to be incorporated by reference herein and as though fully set forth.

Modifications and improvements of the embodiments specifically disclosed herein are within the scope of the following claims. Without further elaboration, it is believed that one skilled in the area can, using the preceding description, utilize the present disclosure to its fullest extent. Therefore the Examples herein are to be construed as merely illustrative and not a limitation of the scope of the present invention in any way. The embodiments disclosed in which an exclusive property or privilege is claimed are defined as follows.

The invention claimed is:

1. A method of improving cognitive function in a subject with Down syndrome, comprising administering to the subject a 5-HT$_6$ receptor antagonist in an amount sufficient for a therapeutic effect by binding to a 5-HT$_6$ receptor, wherein the subject has chronic cognitive impairment caused by a genetic anomaly, wherein the 5-HT$_6$ receptor antagonist is an effective amount of a compound having a structure according to Formula I:

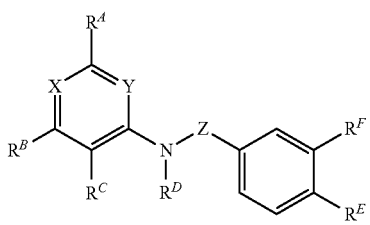

Formula I wherein, for compounds having a structure according to Formula I:
R$^A$ is selected from —H, —NH$_2$, —NH(alkyl), —N(alkyl)$_2$, —NH(aryl), —N(aryl)$_2$, —N(aryl)(alkyl), —NH-heterocycle, or —NH-heterocycloalkyl, where, in the case of —N(alkyl)$_2$ or —N(aryl)$_2$, the alkyl groups or the aryl groups can be identical or different;
R$^B$ is selected from —H, —NH$_2$, —NH(alkyl), —N(alkyl)$_2$, —NH(aryl), —N(aryl)$_2$, —N(aryl)(alkyl), —NH-heterocycle, or —NH-heterocycloalkyl, where, in the case of —N(alkyl)$_2$ or —N(aryl)$_2$, the alkyl groups or the aryl groups can be identical or different;
R$^C$ is selected from —H, —OH, —O(alkyl), —O(aryl), -halogen, -alkyl, or haloalkyl;
R$^D$ is selected from —H, -alkyl, -halogen, -haloalkyl, or -aryl;
R$^E$ is selected from —H, -halogen, —OH, —O(alkyl), —NH$_2$, —NH(alkyl), or —N(alkyl)$_2$, where, in the case of —N(alkyl)$_2$, the alkyl groups can be identical alkyl chains or can be of different length alkyl chains;
R$^F$ is —H, —NH$_2$, —NH(alkyl), —N(alkyl)$_2$, —NH(aryl), —N(aryl)$_2$, —N(aryl)(alkyl), —NH-heterocycle, or —NH-heterocycloalkyl, where, in the case of a dialkyl or diaryl nitrogen the alkyl groups or the aryl groups can be identical or different;
X and Y are independently —N— or —C(H)—; and
Z is selected from —CH$_2$—, —CHX—, —CX$_2$—, —CH(alkyl)-, —CH(aryl)-, —C(aryl)(alkyl)-, —C(alkyl)$_2$-, —C(aryl)$_2$-, —O—, —S—, —S(=O)—, or —S(=O)$_2$—, where X is a halogen and where, in the case of —C(alkyl)$_2$- or —C(aryl)$_2$-, the alkyl groups or aryl groups can be identical or different;
and pharmaceutically acceptable hydrates, solvates, tautomers, salts, and complexes thereof.

2. The method of claim 1, wherein the route of administration of the 5-HT$_6$ antagonist is selected from at least one of the following: intravenous, intraperitoneal, subcutaneous, parenteral, intramuscular, oral, topical, transmucosal, intraventricular, or intrathecal administration.

3. The method of claim 1, wherein the subject suffers from a comorbid disorder associated with Down syndrome comprising Autism spectrum disorders, attention deficit hyperactivity disorder, obsessive compulsive disorder, and disorders involving speech and language.

4. A method of improving cognitive function in a subject with Down syndrome, comprising administering to the subject a 5-HT$_6$ receptor antagonist in an amount sufficient for a therapeutic effect by binding to a 5-HT$_6$ receptor, wherein:
    (i) the 5-HT$_6$ receptor antagonist is a small molecule 5-HT$_6$ receptor antagonist;
    (ii) the small molecule 5-HT$_6$ receptor antagonist has a molecular weight of less than 800 Daltons; and
    (iii) the subject has chronic cognitive impairment caused by a genetic anomaly,
    wherein the 5-HT$_6$ antagonist is an effective amount of compound 7, having the chemical formula:

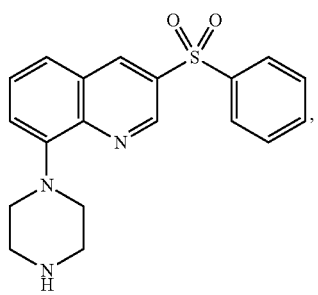

Compound 7 or pharmaceutically acceptable hydrates, solvates, tautomers, salts, and complexes thereof.

5. The method of claim 4, wherein the 5-HT$_6$ antagonist is administered in combination with another therapeutic agent.

6. The method of claim 5, wherein the 5-HT$_6$ antagonist is administered in combination with a cholinesterase inhibitor or an acetylcholine receptor agonist.

7. The method of claim 1, wherein the 5-HT$_6$ antagonist is administered in combination with another therapeutic agent.

8. The method of claim 7, wherein the 5-HT$_6$ antagonist is administered in combination with a cholinesterase inhibitor or an acetylcholine receptor agonist.

9. The method of claim 1, wherein the subject is administered a pharmaceutical composition comprising a 5-HT$_6$ receptor antagonist or a pharmaceutically acceptable salt thereof, and a pharmaceutically acceptable carrier.

10. A method of improving cognitive function in a subject with Down syndrome, comprising administering to the subject a 5-HT$_6$ receptor antagonist in an amount sufficient for a therapeutic effect by binding to a 5-HT$_6$ receptor, wherein the subject has chronic cognitive impairment caused by a genetic anomaly, wherein the 5-HT$_6$ receptor antagonist is an effective amount of a compound having a structure according to Formula II:

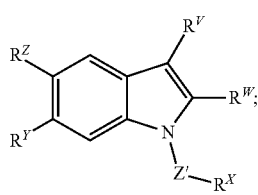

Formula II wherein, for compounds having a structure according to Formula II:
- $R^Z$ is selected from —H, —OH, —O(alkyl), —O(aryl)-O—S-phenyl, —O—S(═O)-phenyl, —O—S(═O)$_2$-phenyl, —O—S-alkyl, —O—S(═O)-alkyl, —O—S(═O)$_2$-alkyl, —O—S-haloalkyl, —O—S(═O)-haloalkyl, —O—S(═O)$_2$-haloalkyl, —O—S-2,6-dihalophenyl, —O—S(═O)-2,6-dihalophenyl, or —OS(═O)$_2$-2,6-dihalophenyl;
- $R^Y$ is selected from —H, -halogen, —NH$_2$, —NH(alkyl), —N(alkyl)$_2$, —NH(aryl), —N(aryl)$_2$, —N(aryl)(alkyl), —NH-heterocycle, or —NH-heterocycloalkyl, where, in the case of —N(alkyl)$_2$ or —N(aryl)$_2$, the alkyl groups or the aryl groups can independently be identical or different;
- $R^W$ is selected from —H, —OH, —O(alkyl), —O(aryl), -halogen, -alkyl, or haloalkyl;
- $R^V$ is selected from —H, -2-ethyl-NH(alkyl), -2-ethyl-N(alkyl)$_2$, -2-ethyl-NH(aryl), -2-ethyl-NH(arylalkyl), -2-ethyl-NH(benzyl), -2-ethyl-NH(alkoxybenzyl), -2-ethyl-NH(haloalkoxybenzyl), -2-ethyl-NH(m-haloalkoxybenzyl), -2-ethyl-N(aryl)$_2$, -2-ethyl-N(alkyl)(aryl), -3-propyl-NH(alkyl), -3-propyl-N(alkyl)$_2$, -3-propyl-NH(aryl), -3-propyl-N(aryl)$_2$, -3-propyl-N(aryl)(alkyl), —NH-heterocycle, or —NH-heterocycloalkyl, where, in the case of a dialkyl or diaryl nitrogen, the alkyl groups or the aryl groups can be identical or different;
- $Z'$ is selected from —H, —CH$_2$—, —CHX—, —CX$_2$—, —CH(alkyl)-, —CH(aryl)-, —C(aryl)(alkyl)-, —C(alkyl)$_2$-, —C(aryl)$_2$-, —O—, —S—, —S(═O)—, or —S(═O)$_2$—, where X is a halogen and where, in the case of —C(alkyl)$_2$- or —C(aryl)$_2$-, the alkyl groups or the aryl groups can be identical or different; and
- $R^X$ is optionally present, and if present is selected from —H, —OH, —O(alkyl), —O(aryl), -halogen, -alkyl, -haloalkyl, or -aryl;

and pharmaceutically acceptable hydrates, solvates, tautomers, salts, and complexes thereof.

11. The method of claim 10, wherein the 5-HT$_6$ antagonist is administered in combination with another therapeutic agent.

12. The method of claim 11, wherein the 5-HT$_6$ antagonist is administered in combination with a cholinesterase inhibitor or an acetylcholine receptor agonist.

13. The method of claim 10, wherein the subject is administered a pharmaceutical composition comprising a 5-HT$_6$ receptor antagonist or a pharmaceutically acceptable salt thereof, and a pharmaceutically acceptable carrier.

14. The method of claim 1, where the 5-HT$_6$ receptor antagonist is chosen from: a 5-HT$_6$ receptor inverse agonist, a 5-HT$_6$ receptor competitive antagonist, or a 5-HT$_6$ receptor inhibitor.

15. The method of claim 14, wherein the 5-HT$_6$ receptor antagonist is a 5-HT$_6$ receptor competitive antagonist.

16. The method of claim 1, wherein the 5-HT$_6$ receptor antagonist directly binds to the 5-HT$_6$ receptor.

17. The method of claim 4, wherein the subject is administered a pharmaceutical composition comprising a 5-HT$_6$ receptor antagonist or a pharmaceutically acceptable salt thereof, and a pharmaceutically acceptable carrier.

18. The method of claim 7, wherein the 5-HT$_6$ antagonist is administered in combination with a cholinesterase inhibitor.

19. The method of claim 18, wherein the cholinesterase inhibitor is selected from at least one of: physostigmine, galantamine, pyridostigmine, or neostigmine.

20. The method of claim 7, wherein the 5-HT$_6$ antagonist is administered in combination with an acetylcholine receptor agonist.

* * * * *